US008663917B2

(12) United States Patent
Wigler et al.

(10) Patent No.: US 8,663,917 B2
(45) Date of Patent: Mar. 4, 2014

(54) USE OF REPRESENTATIONS OF DNA FOR GENETIC ANALYSIS

(75) Inventors: Michael Wigler, Cold Spring Harbor, NY (US); Robert Lucito, Mineola, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 11/094,565

(22) Filed: Mar. 30, 2005

(65) Prior Publication Data

US 2005/0266444 A1 Dec. 1, 2005

Related U.S. Application Data

(60) Division of application No. 09/561,881, filed on May 1, 2000, now abandoned, which is a continuation-in-part of application No. PCT/US98/23168, filed on Oct. 30, 1998.

(60) Provisional application No. 60/064,358, filed on Oct. 30, 1997.

(51) Int. Cl.

| | |
|---|---|
| ***C12Q 1/68*** | (2006.01) |
| ***C12P 19/34*** | (2006.01) |
| *C07H 21/02* | (2006.01) |
| *C07H 21/04* | (2006.01) |

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| | | | |
|---|---|---|---|
| 5,436,142 A | 7/1995 | Wigler et al. | |
| 5,445,934 A | 8/1995 | Fodor et al. | |
| 5,474,796 A | 12/1995 | Brennan | |
| 5,501,964 A | 3/1996 | Wigler et al. | |
| 5,510,270 A | 4/1996 | Fodor et al. | |
| 5,569,753 A | 10/1996 | Wigler et al. | |
| 5,573,933 A | 11/1996 | Seamark et al. | |
| 5,665,549 A | 9/1997 | Pinkel et al. | |
| 5,710,000 A | 1/1998 | Gingeras et al. | |
| 5,721,098 A | 2/1998 | Pinkel et al. | |
| 5,830,645 A | 11/1998 | Pinkel et al. | |
| 5,858,671 A | 1/1999 | Jones | |
| 5,871,917 A | 2/1999 | Duffy | |
| 5,876,929 A | 3/1999 | Wigler et al. | |
| 6,013,431 A | 1/2000 | Soederlund et al. | |
| 6,040,138 A | 3/2000 | Lockhart et al. | |
| 6,100,030 A * | 8/2000 | McCasky Feazel et al. | 435/6 |
| 6,119,120 A | 9/2000 | Miller et al. | |
| 6,153,379 A | 11/2000 | Caskey et al. | |
| 6,159,685 A | 12/2000 | Pinkel et al. | |
| 6,159,713 A | 12/2000 | Wigler et al. | |
| 6,277,606 B1 | 8/2001 | Wigler et al. | |
| 6,287,825 B1 | 9/2001 | Weissman et al. | |
| 6,350,576 B1 | 2/2002 | Wigler et al. | |
| 6,355,423 B1 | 3/2002 | Rothberg et al. | |
| 6,361,947 B1 * | 3/2002 | Dong et al. | 435/6 |
| 6,465,182 B1 | 10/2002 | Gray et al. | |
| 6,528,256 B1 * | 3/2003 | Lin et al. | 435/6.16 |
| 6,562,565 B1 | 5/2003 | Pinkel et al. | |
| 2004/0137473 A1 | 7/2004 | Wigler | |
| 2004/0197774 A1 | 10/2004 | Wigler | |
| 2005/0032095 A1 | 2/2005 | Wigler | |
| 2005/0196799 A1 | 9/2005 | Wigler | |
| 2005/0266444 A1 | 12/2005 | Wigler | |
| 2007/0207481 A1 | 9/2007 | Wigler | |

FOREIGN PATENT DOCUMENTS

| | | |
|---|---|---|
| AU | 753505 | 10/1998 |
| EP | 0 408 918 | 1/1991 |
| EP | 0 721 987 A1 | 7/1996 |
| EP | 1032705 | 5/1999 |
| WO | WO 89/10977 | 11/1989 |
| WO | WO 93/06239 * | 4/1993 |
| WO | WO/94/11383 | 5/1994 |
| WO | WO 96/07917 | 3/1996 |
| WO | WO/96/19589 | 6/1996 |
| WO | WO/97/22721 | 6/1997 |
| WO | WO 98/28438 | 7/1998 |
| WO | WO 99/05321 | 2/1999 |
| WO | WO 99/23256 | 5/1999 |
| WO | WO 99/39001 | 8/1999 |
| WO | WO 00/24939 | 5/2000 |
| WO | WO/01/83822 | 11/2001 |
| WO | WO/2005/035792 | 4/2005 |
| WO | WO/2007/070640 | 6/2007 |
| WO | WO/2008/016374 A2 | 2/2008 |

OTHER PUBLICATIONS

Lisitsyn et al. PNAS vol. 92:151-155. 1995.*
Lucito et al. PNAS vol. 95:4487-4492. Apr. 1998.*
Beaucage, S.L., Curr. Med. Chem., vol. 8, pp. 1213-1244 (2001).*
Danna, K. et al., PNAS USA, vol. 68, pp. 2913-2917 (1971).*
Chang et al., 1998, "Characterization of transformation related genes in oral cancer cells," *Oncogene* 16:1921-1930.
Geng et al., 1998, "Isolation of Differentially Expressed Genes by Combining Representational Diference Analysis (RDA) and cDNA Library Arrays," *BioTechnioues* 25(3):434-438.
Guo et al., 1994, "Direct fluorescence analysis of genetic polymorphisms by hybridization with oligonucleotide arrays on glass supports," *Nucleic Acids Research* 22(24):5456-5465.
Hubank et al., 1994, "Identifying differences in mRNA expression by representational difference analysis of cDNA," *Nucleic Acids Research* 22(25):5640-5648.

(Continued)

*Primary Examiner* — Teresa E Strzelecka
(74) *Attorney, Agent, or Firm* — Gary J. Gershik; Cooper & Dunham LLP

(57) ABSTRACT

It is an object of the present invention to provide a solution to problems associated with the use of microarray technology for the analysis DNA. The present invention provides compositions and methods for the use of simple and compound representations of DNA in microarray technology. The present invention is also directed to methods for the production of High Complexity Representations (HCRs) of the DNA from cells.

15 Claims, 15 Drawing Sheets

(56) References Cited

OTHER PUBLICATIONS

Figure 1:
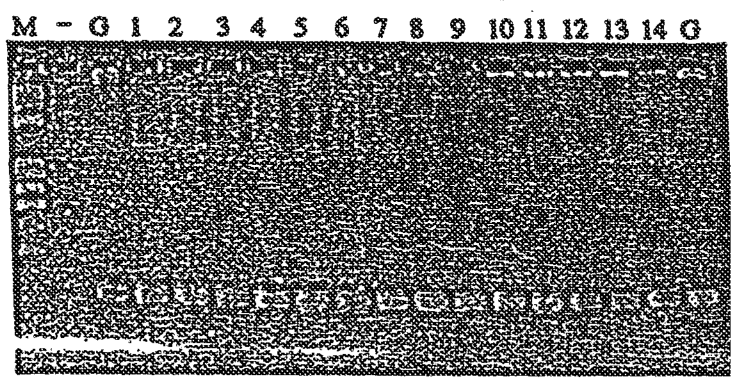
Figure 1:
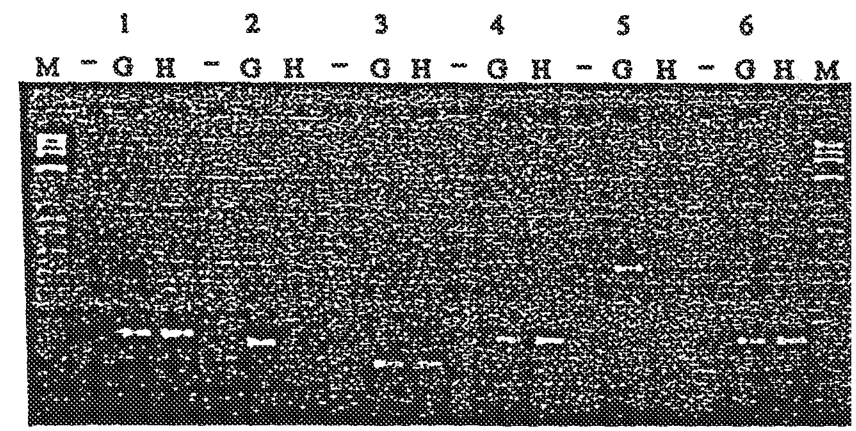

Lisitsyn et al., 1995, "Direct isolation of polymorphic markers linked to a trait by genetically directed representational difference analysis," *Nature Genetics* 6:57-63.
Lisitsyn, et al., "Cloning the Differences Between Two Complex Genomes," *Science*, vol. 259, 1993, 946-951.
Lisitsyn, et al., "Representational difference analysis: finding the differences between genomes," *TIG*, 1995, vol. 11 No. 8, 303-307.
Lucito et al., "Genetic analysis using genomic representations," *Proc. Natl. Acad. Sci. USA*, 1998, 95(8):4487-92.
Lucito et al., "Detecting gene copy number fluctuations in tumor cells by microarray analysis of genomic representations," *Genome Res.*, 2000, 10(11):1726-36.
Oroskar et al., "Detection of immobilized amplicons by ELISA-like techniques," Clin. Chem., 1996, 42(9):1547-55.
Pastinen et al., "Minisequencing: A specific tool for DNA analysis and Diagnostics on oligonucleotide arrays," *Genome Res.*, 1997 7(6):606-14.
Pinkel, et al., "High resolution analysis of DNA copy number variation using comparative genomic hybridization of microarrays," *Nat. Gen.*, 1998, 20:207-211.
Pollack, et al. "Genome-wide analysis of DNA copy-number changes using cDNA microarrays", *Nat. Gen.*, 1999, 23:41-46.
Shepherd, "Preparation and screening of an arrayed human genomic library generated with the P1 cloning system," *Proc. Natl. Acad. Sci. USA*, 1994, vol. 91, 2629-2633.
Vos, et al., "AFLP: a new technique for DNA fingerprinting," *Nucleic Acids Research*, 1995, vol. 23, No. 21, 4407-4414.
Welford, "Detection of differentially expressed genes in primary tumor tissues using representational differences analysis couples to microarray hybridization," *Nucleic Acids Resarch*, 1998, vol. 26, No. 12, 3059-3065.
Schena et al., "Quantitative Monitoring of Gene Expression Patterns with a complementary DNA microarray," *Science*, 270:467-470 (1995).
Shalon et al., "A DNA microarray system for analyzing complex DNA samples using two-color fluorescent probe hybridization," *Genome Research*, 6:639-645 (1996).
Requirement for Restriction/Election issued Feb. 1, 2001 in connection with U.S. Appl. No. 09/561,881, filed May 1, 2000.
Non-Final Office Action issued May 17, 2001 in connection with U.S. Appl. No. 09/561,881, filed May 1, 2000.
Final Office Action issued Feb. 11, 2002 in connection with U.S. Appl. No. 09/561,881, filed May 1, 2000.
Advisory Action issued Jul. 9, 2002 in connection with U.S. Appl. No. 09/561,881, filed May 1, 2000.
Requirement for Restriction/Election issued Jan. 13, 2003 in connection with U.S. Appl. No. 09/561,881, filed May 1, 2000.
Non-Final Office Action issued Apr. 21, 2003 in connection with U.S. Appl. No. 09/561,881, filed May 1, 2000.
Final Office Action issued Nov. 19, 2003 in connection with U.S. Appl. No. 09/561,881, filed May 1, 2000.
Examiner Interview Summary Record issued Jan. 8, 2004 in connection with U.S. Appl. No. 09/561,881, filed May 1, 2000.
Final Office Action issued Jan. 8, 2004 in connection with U.S. Appl. No. 09/561,881, filed May 1, 2000.
Examiner Interview Summary Record issued Feb. 17, 2004 in connection with U.S. Appl. No. 09/561,881, filed May 1, 2000.
Non-Final Office Action issued Mar. 18, 2004 in connection with U.S. Appl. No. 09/561,881, filed May 1, 2000.
Non-Final Office Action issued Aug. 17, 2004 in connection with U.S. Appl. No. 09/561,881, filed May 1, 2000.
Examiner Interview Summary Record issued Feb. 8, 2005 in connection with U.S. Appl. No. 09/561,881, filed May 1, 2000.
Final Office Action issued Apr. 19, 2005 in connection with U.S. Appl. No. 09/561,881, filed May 1, 2000.
Advisory Action issued Sep. 14, 2005 in connection with U.S. Appl. No. 09/561,881, filed May 1, 2000.
Non-Final Office Action issued Dec. 14, 2005 in connection with U.S. Appl. No. 09/561,881, filed May 1, 2000.
Examiner Interview Summary Record issued May 17, 2006 in connection with U.S. Appl. No. 09/561,881, filed May 1, 2000.
Final Office Action issued Aug. 28, 2006 in connection with U.S. Appl. No. 09/561,881, filed May 1, 2000.
Examiner Interview Summary Record issued Jan. 10, 2007 in connection with U.S. Appl. No. 09/561,881, filed May 1, 2000.
Advisory Action issued Mar. 21, 2007 in connection with U.S. Appl. No. 09/561,881, filed May 1, 2000.
Non-Final Office Action issued Jun. 13, 2007 in connection with U.S. Appl. No. 09/561,881, filed May 1, 2000.
Examiner Interview Summary Record issued Dec. 27, 2007 in connection with U.S. Appl. No. 09/561,881, filed May 1, 2000.
Final Office Action issued Mar. 13, 2008 in connection with U.S. Appl. No. 09/561,881, filed May 1, 2000.
Non-Final Office Action issued Mar. 5, 2009 in connection with U.S. Appl. No. 09/561,881, filed May 1, 2000.
Examiner Interview Summary Record issued Apr. 1, 2009 in connection with U.S. Appl. No. 09/561,881, filed May 1, 2000.
Examiner Interview Summary Record issued Apr. 14, 2009 in connection with U.S. Appl. No. 09/561,881, filed May 1, 2000.
Non-Final Office Action issued Aug. 13, 2004 in connection with U.S. Appl. No. 10/677,396, filed Oct. 1, 2003.
Final Office Action issued Apr. 20, 2005 in connection with U.S. Appl. No. 10/677,396, filed Oct. 1, 2003.
Notice of Abandonment issued Nov. 1, 2005 in connection with U.S. Appl. No. 10/677,396 filed Oct. 1, 2003.
Non-Final Office Action issued Jul. 3, 2007 in connection with U.S. Appl. No. 11/094,388, filed Mar. 30, 2005.
Final Office Action issued Apr. 8, 2008 in connection with U.S. Appl. No. 11/094,388, filed Mar. 30, 2005.
Notice of Allowance Issued Dec. 30, 2008 in connection with U.S. Appl. No. 11/094,388, filed Mar. 30, 2005.
Issue Notification Issued Apr. 22, 2009 in connection with U.S. Appl. No. 11/094,388, filed Mar. 30, 2005.
Notification of Transmittal of International Preliminary Examination Report, issued Mar. 9, 2000, in connection with International Application No. PCT/US98/23168.
Notification of Transmittal of International Search Report or the Declaration, issued Feb. 8, 1999, in connection with International Application No. PCT/US98/23168.
Written Opinion, issued Oct. 29, 1999, in connection with International Application No. PCT/US98/23168.
Examiner's First Report, issued Oct. 11, 2001, in connection with Australian Application No. 753505.
Letters Patent documents issued Feb. 6, 2003 in connection with Australian Patent Application No. 753505.
Official Action issued Jun. 20, 2006 in connection with Canadian Application No. 2,307,674.
Official Action issued Jul. 4, 2007 in connection with Canadian Application No. 2,307,674.
Official Action issued May 20, 2008 in connection with Canadian Application No. 2,307,674.
Supplementary European Search Report, issued Aug. 3, 2004, in connection with European Patent Application No. EP 98958453.7.
Communication Pursuant to Article 96(2) EPC issued May 4, 2005 in connection with European application 98958453.7.
Communication Pursuant to Article 96(2) EPC issued Aug. 27, 2007 in connection with European application 98958453.7.
Invitation Pursuant to Article 94(3) and Rule 71(1) EPC issued Oct. 8, 2008 in connection with European application 98958453.7.
Official Action issued Aug. 19, 2008 in connection with Japanese Application No. 2000-519111.
Official Action issued Mar. 17, 2009 in connection with Japanese Application No. 2000-519111.
International Search Report, issued Dec. 12, 2002, in connection with International Application No. PCT/US01/13949.
Notification of Transmittal of International Preliminary Examination Report, issued Mar. 25, 2003, in connection with PCT/US/01/13949.
International Search Report issued Apr. 20, 2003 in connection with PCT/US/01/13949.
Barrett, M.T. et al. Genotypic analysis of multiple loci in somatic cells by whole genome amplification. Nucleic Acids Res. Sep. 11, 1995;23(17):3488-92.

(56) References Cited

OTHER PUBLICATIONS

Bishop, D.T. et al. A model for restriction fragment length distributions. Am J Hum Genet. Sep. 1983;35(5):795-815.
Cheung, V.G. et al. Whole genome amplification using a degenerate oligonucleotide primer allows hundreds of genotypes to be performed on less than one nanogram of genomic DNA. Proc Natl Acad Sci U S A. Dec. 10, 1996;93(25):14676-9.
Dong, S., et al. Flexible use of high-density oligonucleotide arrays for single-nucleotide polymorphism discovery and validation. Genome Res. Aug. 2001;11(8):1418-24.
Heller, R.A. et al. Discovery and analysis of inflammatory disease-related genes using cDNA microarrays. Proc Natl Acad Sci U S A. Mar. 18, 1997;94(6):2150-5.
Houldsworth, J. et al. Comparative genomic hybridization: an overview. Am J Pathol. Dec. 1994;145(6):1253-60.
Li, F., et al. Selection of optimal DNA oligos for gene expression arrays. Bioinformatics. Nov. 2001;17(11):1067-76.
Paunio, T. et al. Preimplantation diagnosis by whole-genome amplification, PCR amplification, and solid-phase minisequencing of blastomere DNA. Clin Chem. Sep. 1996;42(9):1382-90.
Sekizawa, A. et al. Prenatal diagnosis of the fetal RhD blood type using a single fetal nucleated erythrocyte from maternal blood. Obstet Gynecol. Apr. 1996;87(4):501-5.
Sermon, K. et al. Adaptation of the primer extension preamplification (PEP) reaction for preimplantation diagnosis: single blastomere analysis using short PEP protocols. Mol Hum Reprod. Mar. 1996;2(3):209-12.
Tengan, C.H. et al Detection and analysis of mitochondrial DNA deletions by whole genome PCR. Biochem Mol Med. Jun. 1996;58(1):130-4.
International Preliminary Examination Report issued Apr. 24, 2003 in connection with PCT/US/01/13949.
Armengol, G. et al. Recurrent gains of 1q, 8 and 12 in the Ewing family of tumours by comparative genomic hybridization. Br J Cancer. 1997;75(10):1403-9.
Barrett, M.T. et al. Determination of the frequency of loss of heterozygosity in esophageal adenocarcinoma by cell sorting, whole genome amplification and microsatellite polymorphisms. Oncogene. May 2, 1996;12(9):1873-8.
Hermsen, M.A. et al. Comparative genomic hybridization: a new tool in cancer pathology. Hum Pathol. Apr. 1996;27(4):342-9.
Kallioniemi, O.P. et al. Comparative genomic hybridization: a rapid new method for detecting and mapping DNA amplification in tumors. Semin Cancer Biol. Feb. 1993;4(1):41-6.
Sakamoto, M. et al. CGH (comparative genomic hybridization). Nippon Rinsho. Apr. 1996;54(4):933-43.
Response to Official Action issued Jun. 20, 2006 in connection with Canadian Application No. 2,307,674.
Response to Official Action issued May 20, 2008 in connection with Canadian Application No. 2,307,674.
Response to Communication Pursant to Article 96(2) EPC issued May 4, 2005 in connection with European application 98958453.7.
Response to Invitation Pursant to Article 94(3) and Rule 71(1) EPC issued Oct. 8, 2008 in connection with European application 98958453.7.
Office Action issued Oct. 28, 2009 in connection with U.S. Appl. No. 10/851,779, filed May 21, 2004.
Shoemaker et al., "Experimental annotation of the human genome using microarray technology." Nature vol. 409, p. 922-927, (2001).
Supplemental Amendment In Response to Mar. 5, 2009 Office Action and Summary of Mar. 12, 2010 Examiner Interview filed on Mar. 12, 2010 in connection with U.S. Appl. No. 09/561,881, filed May 1, 2000.
Examiner Interview Summary Record issued Mar. 18, 2010 in connection with U.S. Appl. No. 09/561,881, filed May 1, 2000.
Official Action issued Jan. 19, 2010 in connection with Japanese Application No. 2009-167204.
Amendment in Response to Official Action issued Jan. 19, 2010 in connection with Japanese Application No. 2009-167204.
Official Action issued Jul. 16, 2009 in connection with Canadian Application No. 2,307,674.
Final Office Action issued May 25, 2010 in connection with U.S. Appl. No. 09/561,881, filed May 1, 2000.
Final Office Action issued May 25, 2010 in connection with U.S. Appl. No. 10/851,779, filed May 21, 2004.
Kruglvak et al. (2001), "Variation is the spice of life," Nature Genetics, vol. 27:234-236.
Communication Pursuant to Article 94(3) EPC issued May 6, 2010 in connection with European application 98958453.7.
Response to Communication Pursuant to Article 94(3) EPC issued May 6, 2010 in connection with European application 98958453.7.
Jul. 9, 2010 Amendment in Response to May 25, 2010 Final Office Action submitted in connection with U.S. Appl. No. 10/851,779, filed May 21, 2004.
Jul. 21, 2010 Amendment in Response to May 25, 2010 Final Office Action submitted in connection with U.S. Appl. No. 09/561,881, filed May 1, 2000.
Jul. 28, 2010 Advisory Action issued in connection with U.S. Appl. No. 10/851,779, filed May 21, 2004.
Aug. 2, 2010 Advisory Action issued in connection with U.S. Appl. No. 09/561,881, filed May 1, 2000.
Amendment in Response to Aug. 2, 2010 Advisory Action and May 25, 2010 Final Office Action submitted Aug. 9, 2010 in connection with U.S. Appl. No. 09/561,881, filed May 1, 2000.
Interview Summary issued Aug. 31, 2010 in connection with U.S. Appl. No. 10/851,779, filed May 21, 2004.
Office Action issued Sep. 2, 2010 in connection with U.S. Appl. No. 09/561,881, filed May 1, 2000.
Wodicka, L. et al., Nature Biotechn. vol. 15, pp. 1359-1367 (1997).
DeRisi, J. et al., Nature Genetics, vol. 14, pp. 457-460 (1996).
Soares, M.B. et al., PNAS, vol. 91, pp. 9228-9232 (1994).
Oct. 19, 2010 Supplemental Amendment to Jul. 9, 2010 Amendment, Summary of Aug. 25, 2010 Telephonic Examiner Interview, and Supplemental Information Disclosure Statement filed in connection with U.S. Appl. No. 10/851,779, filed May 21, 2004.
Dec. 2, 2010 Amendment in Response to Sep. 2, 2010 Office Action and Supplemental Information Disclosure Statement submitted in connection with U.S. Appl. No. 09/561,881, filed May 1, 2000.
Feb. 4, 2011 Official Action issued in connection with European Application No. 98958453.7.
Feb. 24, 2011 Final Office Action issued in connection with U.S. Appl. No. 09/561,881, filed May 1, 2000.

* cited by examiner

HCR Complexity

A

Diploid HCR from TumorBiopsies

B

WWW Probe b cycD1

| | High DpnII | Low BglII |
|---|---|---|
| Representation | 5.5 | 6.5 |
| Genomic | 5.1 | 6.4 |

c-erbB2

| | High DpnII | Low BglII |
|---|---|---|
| Representation | 9.2 | 11.3 |
| Genomic | 10.5 | 9.3 |

c-myc

| | High DpnII | Low BglII |
|---|---|---|
| Representation | 5.5 | 7.6 |
| Genomic | 5.2 | 5.2 |

Values represent the ratio of Tumor to Normal

Primary Tumor HCR Panel

BBR3 BBR16 BBR33 BBR38 BBR44 BBR49 BBR50 BBR55
Dpl Anu Dpl Anu Dpl Anu Dpl Anu Dpl Anu Dpl Anu Dpl Anu Dpl Anu

Dpl Anu Dpl Anu Dpl Anu Dpl Anu Dpl Anu Dpl Anu Dpl Anu Dpl Anu
BBR61 BBR66 BBR67 CHTN5 CHTN7 CHTN8 NSBR5 CHTN9

LOH Analysis of HCR

Primary Tumor HCR

\+ + BBR16 BBR31 BBR67 CHTN5 CHTN9 NSBR5

– Gen HCR Dpl Anu Dpl Anu Dpl Anu Dpl Anu Dpl Anu Dpl Anu

USE OF REPRESENTATIONS OF DNA FOR GENETIC ANALYSIS

This application is a division of U.S. application Ser. No. 09/561,881, filed May 1, 2000, which is a continuation-in-part of International Patent Application No. PCT/US98/23168, filed Oct. 30, 1998, which claims benefit of U.S. Provisional Application No. 60/064,358, filed 30 Oct. 1997.

This invention was made with Government support under Contract Nos. 5R35 CA 39829-13 and 5P50 CA 68425-03 awarded by the National Institutes of Health, and under U.S. Army Grant No. DAMD17-94-J-4247. The Government has certain rights to this invention.

1. Field of the Invention

The field of the invention is genetic analysis.

2. Background of the Invention

2.1. Microarray Technology

Although global methods for genomic analysis, such as karyotyping, determination of ploidy, and more recently comparative genomic hybridizaton (CGH) (Feder et al., 1998, *Cancer Genet. Cytogenet.* 102:25-31; Gebhart et al., 1998, *Int. J. Oncol.* 12:1151-1155; Larramendy et al., 1997, *Am. J. Pathol.* 151:1153-1161; Lu et al., 1997, *Genes Chromosomes Cancer* 20:275-281, all of which are incorporated herein by reference) have provided useful insights into the pathophysiology of cancer and other diseases or conditions with a genetic component, and in some instances have aided diagnosis, prognosis and selection of treatment, current methods do not afford a level of resolution of greater than can be achieved by standard microscopy, or about 5-10 megabases. Moreover, while many particular genes that are prone to mutation can be used as probes to interrogate the genome in very specific ways (Ford et al., 1998, *Am. J. Hum. Genet.* 62:676-689; Gebhart et al., 1998, *Int. J. Oncol.* 12:1151-1155; Hacia et al., 1996, *Nat. Genet.* 14:441-447, all of which are incorporated herein by reference), this one-by-one query is an inefficient and incomplete method for genetically typing cells.

With the advent of microarray, or "chip" technology, it is now clearly possible to contemplate obtaining a high resolution global image of genetic changes in cells. Two general approaches can be conceived. One is to profile the expression pattern of the cell using microarrays of cDNA probes (DeRisi et al., 1996, *Nat. Genet.* 14:457-460). This method is very likely to yield useful information about cancer, but suffers limitations. First, the interpretation of the data obtained and its correlation with disease process is likely to be a complex and difficult problem: multiple changes in gene expression will be observed that are not relevant to the disease of interest. Second, our present cDNA collections are not complete, and any chip is likely to be obsolete in the near future. Third, while a picture of the current state of the cell might be obtained, there would be little direct information about how the cell arrived at that state. Lastly, obtaining reliable mRNA from biopsies is likely to be a difficult problem, because RNA is very unstable and undergoes rapid degradation due to the presence of ubiquitous RNAses.

The second approach is to examine changes in the cancer genome itself. DNA is more stable than RNA, and can be obtained from poorly handled tissues, and even from fixed and archived biopsies. The genetic changes that occur in the cancer cell, if their cytogenetic location can be sufficiently resolved, can be correlated with known genes as the data bases of positionally mapped cDNAs mature. Thus, the information derived from such an analysis is not likely to become obsolete. The nature and number of genetic changes, can provide clues to the history of the cancer cell. Finally, a high resolution genomic analysis may lead to the discovery of new genes involved in the etiology of the disease or disorder of interest.

Microarrays typically have many different DNA molecules, often referred to as probes, fixed at defined coordinates, or addresses, on a flat, usually glass, support. Each address contains either many copies of a single DNA probe, or a mixture of different DNA probes, and each DNA molecule is usually 2000 nucleotides or less in length. The DNAs can be from many sources, including genomic DNA or cDNA, or can be synthesized oligonucleotides. For clarity and brevity, we refer to those chips with genomic or cDNA derived probes as DNA chips and those chips with synthesized oligonucleotide probes as oligo chips, respectively. Chips are typically hybridized to samples, applied as single stranded nucleic acids in solution.

The extent of hybridization with samples at a given address is determined by many factors including the concentration of complementary sequences in the sample, the probe concentration, and the volume of sample from which each address is able to capture complementary sequences by hybridization. We refer to this volume as the diffusion volume. Because the diffusion volume, and hence, the potential hybridization signal, may vary from address to address in the hybridization chamber, the probe array is most accurate as a comparator, measuring the ratio of hybridization between two differently labeled specimens (the sample) that are thoroughly mixed and therefore share the same hybridization conditions, including the same diffusion volume. Typically the two specimens will be from diseased and disease free cells.

We distinguish between compound and simple DNA probe arrays based on the nucleotide complexity of the probes at each address. When this nucleotide complexity is less than or equal to about 1.2 kb per address, we speak of simple DNA probe arrays. When it exceeds 1.2 kb per address, we speak of compound probe arrays. Simple probe arrays are currently able to detect cDNA species that are present at 2 to 10 copies of mRNA per cell when contacted with a solution containing a total cDNA concentration of 1 mg/ml. The threshold of detection of a given species is estimated to be in the range of 4 to 20 ng/ml. Because a simple probe array is generally able to capture only a single species of DNA from the sample, this detection threshold poses a problem for the use of simple DNA probe arrays for analysis of genomic DNA. The concentration of a unique 700 bp fragment of human genomic DNA (which has a total complexity of about 3000 mb) in a solution of total genomic DNA dissolved at its maximum concentration of 8 mg/ml would be about 2 ng/ml, just below the lower estimate of the threshold of detection. Hence, in its unaltered format, the simple DNA probe chip would not suffice for the robust detection of genomic sequences.

The compound chip partially addresses this problem by increasing the nucleotide complexity of different probes at a given address, allowing for the capture of several species of DNA fragments at a single address. The signals of the different captured species combine to yield a detectable level of hybridization from genomic DNA. Present forms of compound probe arrays place the insert found in a single clone of a megacloning vector, such as a BAC, at each address. Because each address contains fragments derived from the entire BAC clone, several problems are created. The presence of repeat elements in the genomic inserts requires quenching with cold unlabeled DNA. Also, the great size of the megacloning vector inserts limits the positional resolution. For example, in the case of a compound probe array made of BACs, hybridization to a particular address reveals only to which BAC the hybridizing sequence is complementary, and does not reveal the specific complementary gene or sequence within that BAC. Another drawback is the presence of DNA derived from the megacloning vector and host sequences. The steps of excising and purifying the genomic DNA inserts from the vector and host sequences complicate and hinder rapid fabrication of microarrays.

2.2. Problems Associated with Genetic Analysis

Analysis of the genetic changes in human tumors is often problematic because of the presence of normal stroma. Samples of tumor tissue are often contaminated with non-cancerous cells, making isolation and study of tumor cell DNA difficult. While either microdissection or flow cytometry can produce small samples highly enriched for tumor cells or nuclei, the amount of extracted DNA recoverable from such enriched samples is insufficient for most uses.

One technique which can be used on small samples is representational difference analysis (RDA). (U.S. Pat. No. 5,436,142, Lisitsyn et al., 1993, *Science* 259:946-951) RDA is a subtractive DNA hybridization technique that is useful, e.g., to discover the differences between paired normal and tumor genomes. The first step of RDA requires making an "amplicon representation", which is a highly reproducible simplification and amplification of a DNA population. Typically, an amplicon representation is a set of restriction endonuclease fragments of a limited size range generated by PCR (polymerase chain reaction). PCR generates sufficient amounts of DNA for subsequent processing, on the order of 100 ug, starting from as little as 3 ng of DNA (the amount of DNA isolatable from about 1000 cells).

One limitation of the amplicon useful in RDA is that an amplicon representation with much lower complexity than that of the genome from which the amplicon is derived is needed to enable the subtractive hybridization to proceed effectively. Such low complexity representations (LCRs) do not "capture" enough (typically, 7% or less) of the genome to be generally useful for other applications. The complexity of the representation is related to the frequency of cutting of the restriction enzyme used to generate the genomic fragments, combined with the amplification reaction steps, e.g., PCR, which tend to favor the smaller fragments.

Whole genome amplification (WGA) is a method by which more complex amplifications of the DNA from minute samples are generated. (Sun et al., 1995, *Nucleic Acids Res.* 23(15):3034-3040, Barrett et al., 1995, *Nucleic Acids Res.* 23(17):3488-3492.) In WGA, PCR is performed on DNA isolated from small amounts of sample using random primers.

There are at least three disadvantages to the WGA method:

1. The amplified DNA can not be used for Southern analysis. Because more than one primer can bind to a single gene, a heterogenous mixture of different sized fragments can be generated from a single gene. This would result in a smear, not a band, being detected by Southern hybridization.
2. Due to the random nature of the amplification, each amplification results in a different mixture of fragments. Therefore the amplification is not reliably reproducible. This makes the use of such whole genomic amplifications for the purposes of sample to sample comparisons difficult.
3. Whole genomic amplifications are not useful for quantitating the copy number of genes present in the original sample. Because the primers are random, the representation of each gene can vary greatly with respect to the other genes. Thus, the abundance of each gene relative to other genes in the original sample is not preserved during the amplification, making quantitation of copy number impossible.

Thus, there continues a long felt need for a method of obtaining amounts of genetic material from scant genomic samples to enable genetic analysis of small samples using techniques which previously were inapplicable due to the limited amount of DNA isolatable from such samples. There is also a long felt need for a method of amplifying and storing DNA from scant, nonrenewable sources.

3. SUMMARY OF THE INVENTION

It is an object of the present invention to provide a solution to problems associated with the use of microarray technology for the analysis DNA. The present invention provides compositions and methods for the use of simple and compound representations of DNA in microarray technology. A representation of DNA is a sampling of DNA produced by a restriction endonuclease digestion of genomic or other DNA, followed by linkage of adaptors and then amplification with primers complementary to the adaptors. The DNA may be from any source. Sources from which representations can be made include, but are not limited to, genomic or cDNA from tumor biopsy samples, including breast cancer and prostate cancer biopsies, normal tissue samples, tumor cell lines, normal cell lines, cells stored as fixed specimens, autopsy samples, forensic samples, paleo-DNA samples, microdissected tissue samples, isolated nuclei, and fractionated cell or tissue samples.

Representation of the genome results in a simplification of its complexity; the genomic complexity of a representation can range from below 1% to as high as 95% of the total genome. This simplification allows for desirable hybridization kinetics. Probes from representations of genomic DNA can be used as the probe of the microarray, and as the labeled sample hybridized to any microarray, however derived. Because formation of a representation involves the step of amplifying the DNA via an amplification reaction, such as the polymerase chain reaction, ligase chain reaction, etc., very small amounts of DNA can be used as starting material. The use of compound representations, defined as a representation of a representation, is also provided by the present invention. As is fully described below, compound representations can be used, for example, to screen for polymorphisms.

In addition, representational difference analysis (RDA), can be used for the efficient removal of vector and host sequences when constructing microarrays from megacloning vectors. RDA may also be used to remove any known, unwanted sequences from the representation, including repetitive sequences.

As used herein, the term "simple representation" refers to a sampling of DNA produced by a restriction endonuclease digestion of genomic or other DNA, followed by linkage of adaptors and then amplification with primers complementary to the adaptors.

As used herein, the term "compound representation" refers to a representation of a representation.

The present invention is also directed to methods for the production of High Complexity Representations (HCRs) of the DNA from cells. In one embodiment, the HCR is made by completely digesting a small amount of DNA from any source with a relatively frequent cutting restriction endonuclease, ligating adaptor oligonucleotides to the ends of the resulting fragments, and amplifying the fragments, for example by PCR, using primers to said adaptor oligonucleotides.

In another embodiment, the HCR is made by completely digesting a small amount of DNA from any source with at least two restriction endonucleases, ligating adaptor oligonucleotides to the ends of the resulting fragments, and amplifying the fragments, for example by PCR, using primers to said adaptor oligonucleotides.

HCRs can represent from 20% to 95% of the genome, depending on the restriction enzyme or enzymes used, and the conditions of the PCR amplification.

Sources from which HCR's can be made include, but are not limited to, tumor biopsy samples, including breast cancer and prostate cancer biopsies, normal tissue samples, tumor cell lines, normal cell lines, cells stored as fixed specimens, autopsy samples, forensic samples, paleo-DNA samples, microdissected tissue samples, isolated nuclei, and fractionated cell or tissue samples.

HCRs are useful for, but not limited to, determining gene copy number, deletion mapping, determining loss of heterozygosity, comparative genomic hybridization, and archiving of DNA.

4. BRIEF DESCRIPTION OF THE FIGURES

The present invention may be more fully understood by reference to the following detailed description of the invention, examples of specific embodiments of the invention and the appended figures in which:

FIGS. 1 (A-B) illustrates the results of PCR reactions designed to quantitate the complexity of HCRs. Panel A shows a gel on which the products of PCR reactions have been separated and visualized. The PCR reactions were performed using probes chosen randomly from an assortment of sequence tags, representing sequences known to be present in the human genome. This sequence tag is present in all of the HCRs produced from 14 tumor biopsy normals obtained by sorting (numbered 1-14). M represents the marker ϕx174 HaeIII digested. G denotes two different genomic DNAs used as positive controls, and – denotes a reaction which contained no DNA. Panel B shows the products of reactions performed on HCRs with 6 probes chosen randomly from an assortment of sequence tags, representing sequences known to be present in the human genome. The presence of these sequence tags in genomic DNA (G), HCR (H), and no DNA was tested. The HCR did not contain 2 of the 6 sequence tags assayed, as can be seen by the absence of a band in the HCR lane under the numbers 2 and 5. M represents the marker ϕx174 HaeIII.

Figure 2:
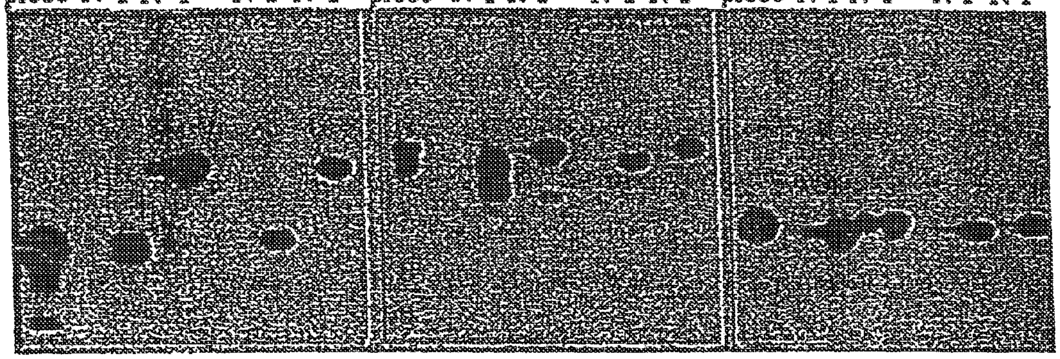

FIGS. 2 (A-B) illustrates an analysis of copy number using low (LCR) and high (HCR) complexity representations and genomic DNA (Genomic) for several amplified loci (cycD1, c-erB2, and c-myc each denoting the respective locus). Panel a is a Southern blot comparing tumor cell lines (T) to normal (N). DpnII represents the HCRs and Bg1II represents the LCRs. The lane marked probe denotes the free probe used as a marker. The probes used for hybridization were derived from small Bg1II fragments isolated from P1 clones specific for each locus respectively. FIG. 2B represents the quantitation of the above described Southern blots comparing the amount of amplification of high and low complexity representations with genomic DNA cut with the same restriction enzyme used to generate each representation.

Figure 3:
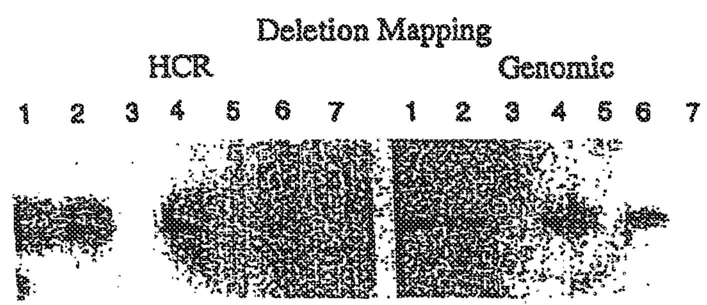

FIG. 3 illustrates the use of HCRs for deletion mapping. Shown is the deletion mapping of 7 tumor cell lines (designated 1-7) which already display a known deletion pattern for several probes from the human genomic region 20p11. The deletion pattern of the DpnII HCRs (denoted HCR) is compared to the DpnII digest of the genomic DNA (denoted Genomic).

Figure 4:
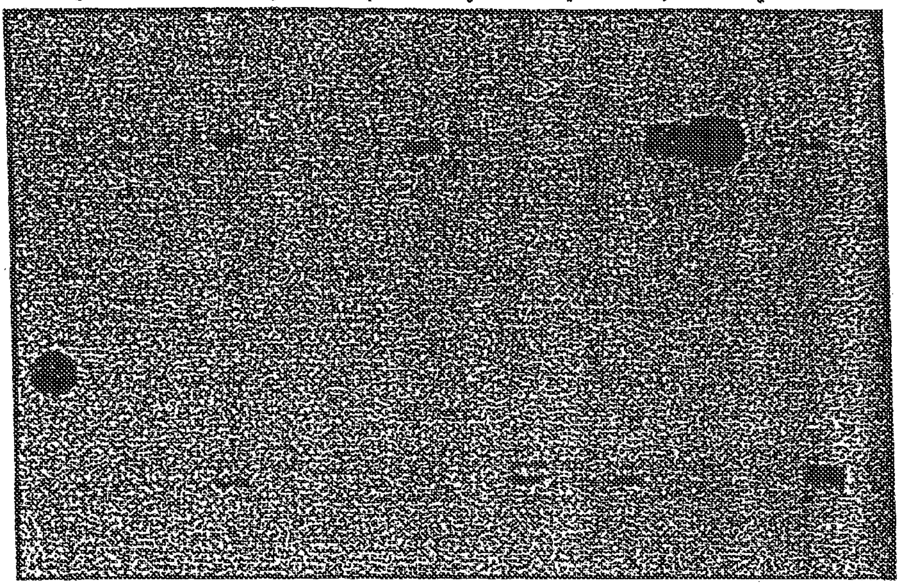

FIG. 4 illustrates a comparison of primary tumor biopsies by HCR Southern blotting analysis. Primary tumor biopsy HCRs (denoted by a number preceded by BBR, CHTN, or NSBR) from matched diploid (Dpl) and aneuploid (Anu) were compared by Southern blot analysis. The c-myc probe which was hybridized was the same as that used in FIG. 2.

Figure 5:
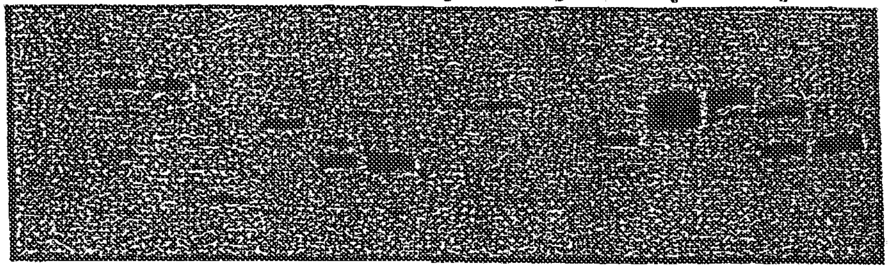

FIG. 5 illustrates the use of HCRs for LOH analysis. Shown is LOH analysis carried out on HCRs derived from sorted primary tumor biopsies, where Dpl denotes diploid and Anu denotes aneuploid. The primers used in the reaction amplify a fragment from the p53 locus which contains a tetranucleotide repeat. +Gen denotes a mixed population normal genomic DNA which was used as positive control and +HCR denotes the HCR produced from this mixed normal genomic DNA. –lane represents a reaction which no template was added.

Figure 6:
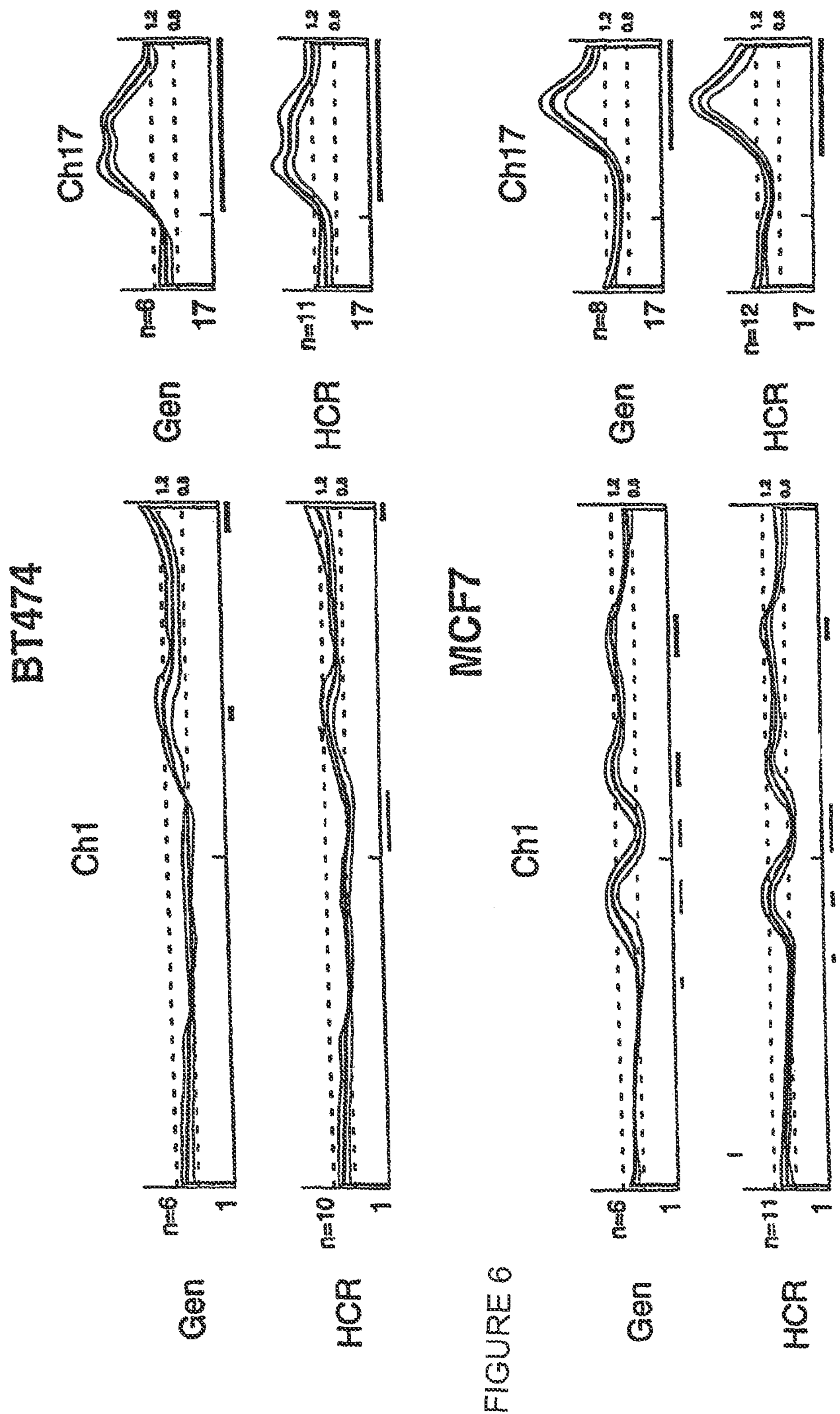

FIG. 6 illustrates the use of HCRs for comparative genomic hybridization. Shown are two representative chromosome spreads (Ch 1, and Ch 17) comparing the genomic (Gen) to the HCR, for two different cell lines, BT474, and MCF7. Lines below the spreads denote differences which exceed the standard deviation, suggesting an abnormal copy number.

FIGS. 7 A-C graphically depict the results of microarray experiments graphed such that the intensity of one channel (usually the Cy3 channel) is the abscissa and the ratio of Cy5 to Cy3 is the ordinate.

Figure 8:
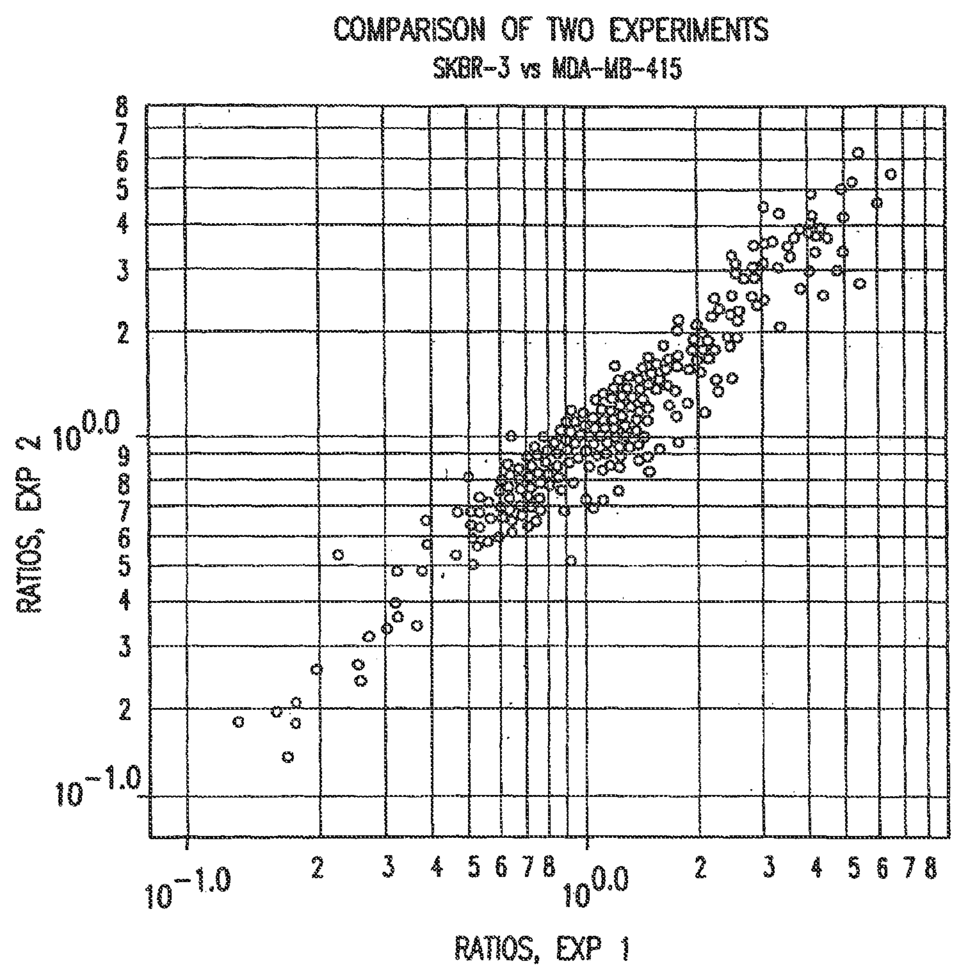

FIG. 8 graphically depicts the comparison of two microarray experiments performed with parallel representations produced from the two cell lines MDA-MB-415 and SKBR-3.

Figure 9:
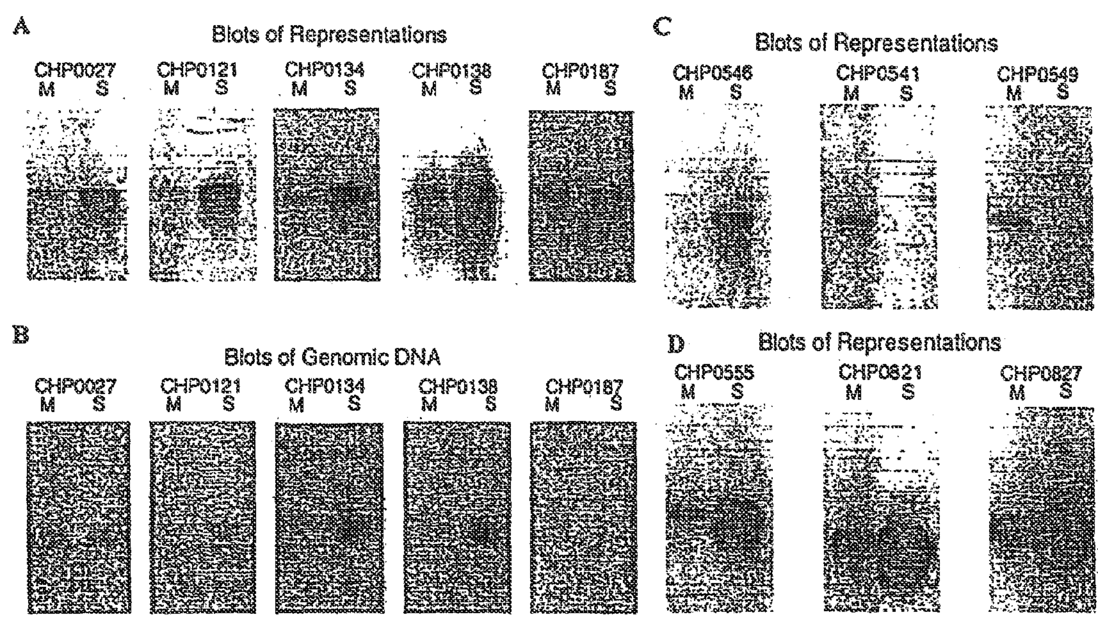

FIGS. 9 A-D illustrate the analysis of 36 probes that displayed copy number differences from the previous experiment shown in FIG. 2 by Southern blotting representations and genomic DNA from the two cell lines MDA-MB-415 and SKBR-3.

Figure 10:
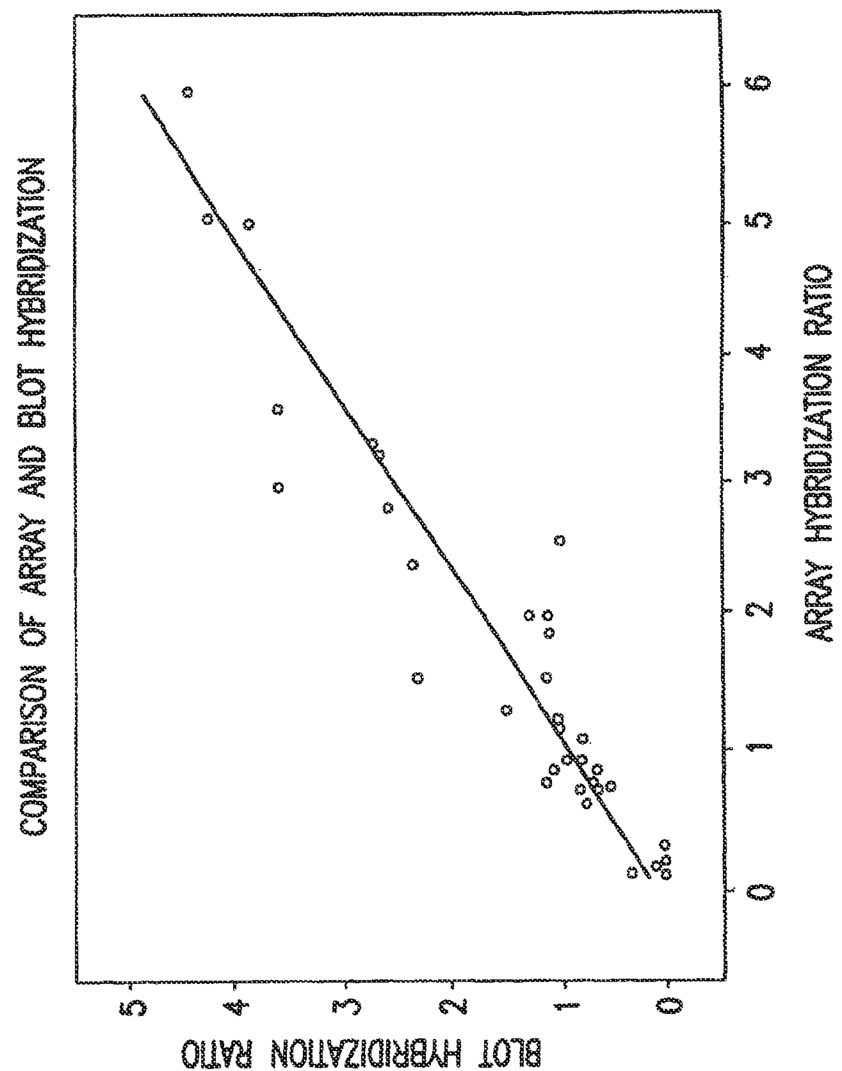

FIG. 10 shows the ratios of gene copy number obtained by microarray measurement on the x-axis with ratios obtained by quantitative blotting of representations on the y-axis.

Figure 11A:
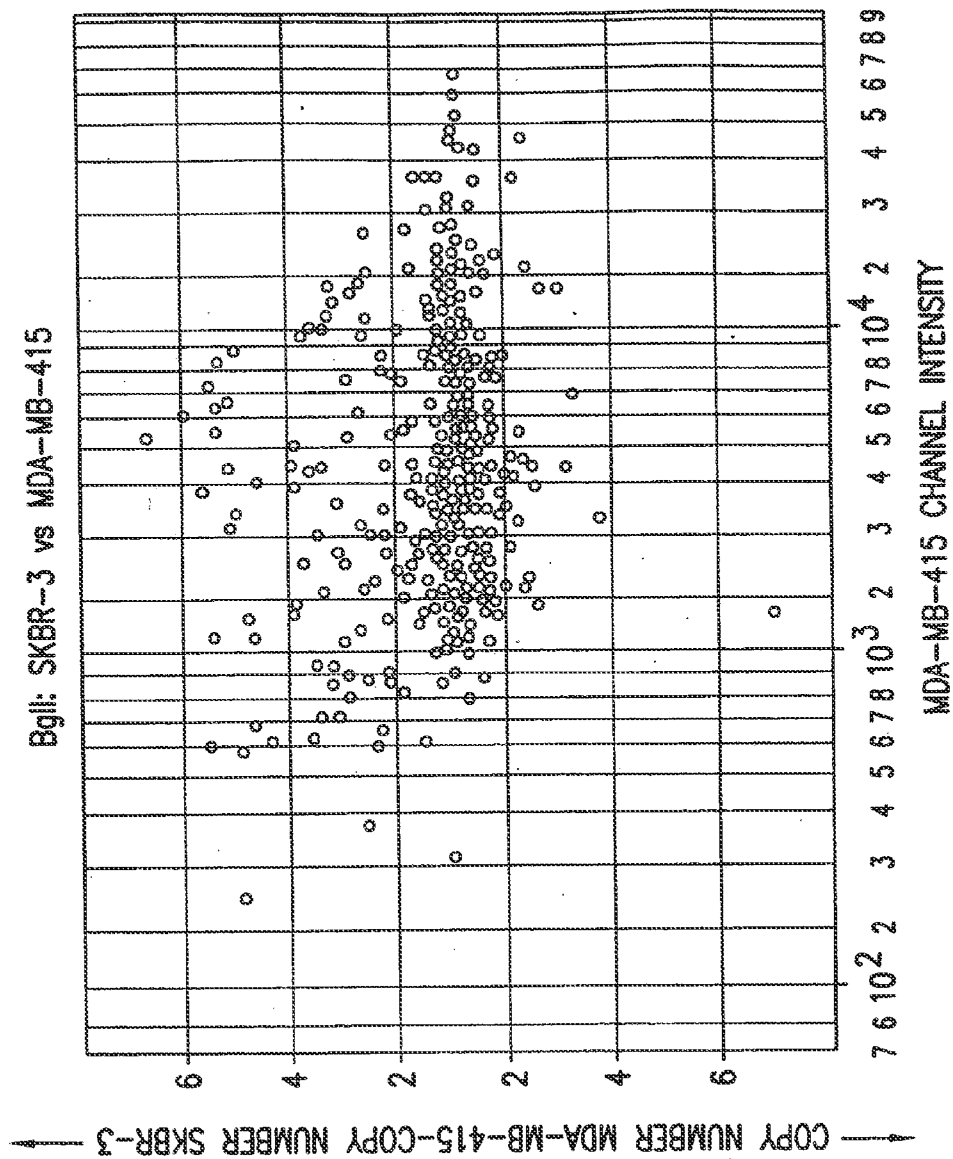
Figure 11B:
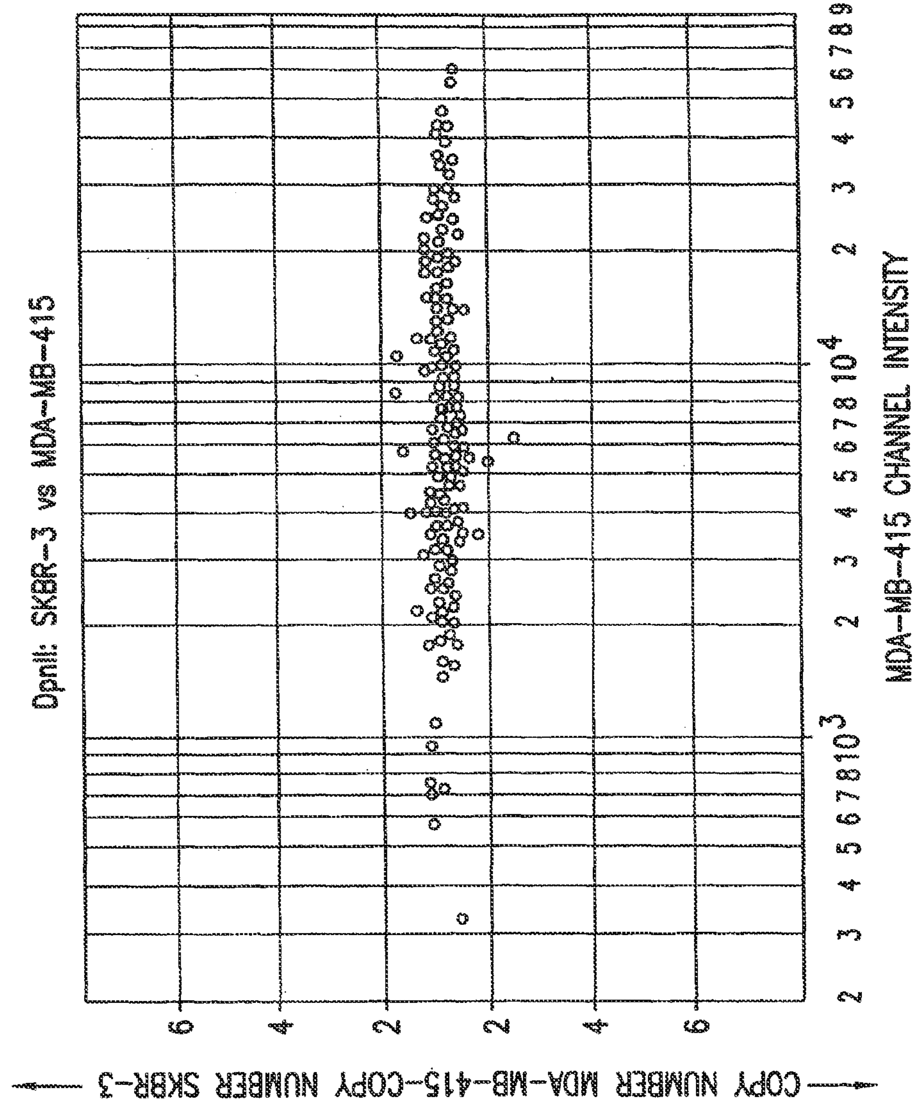
Figure 11C:
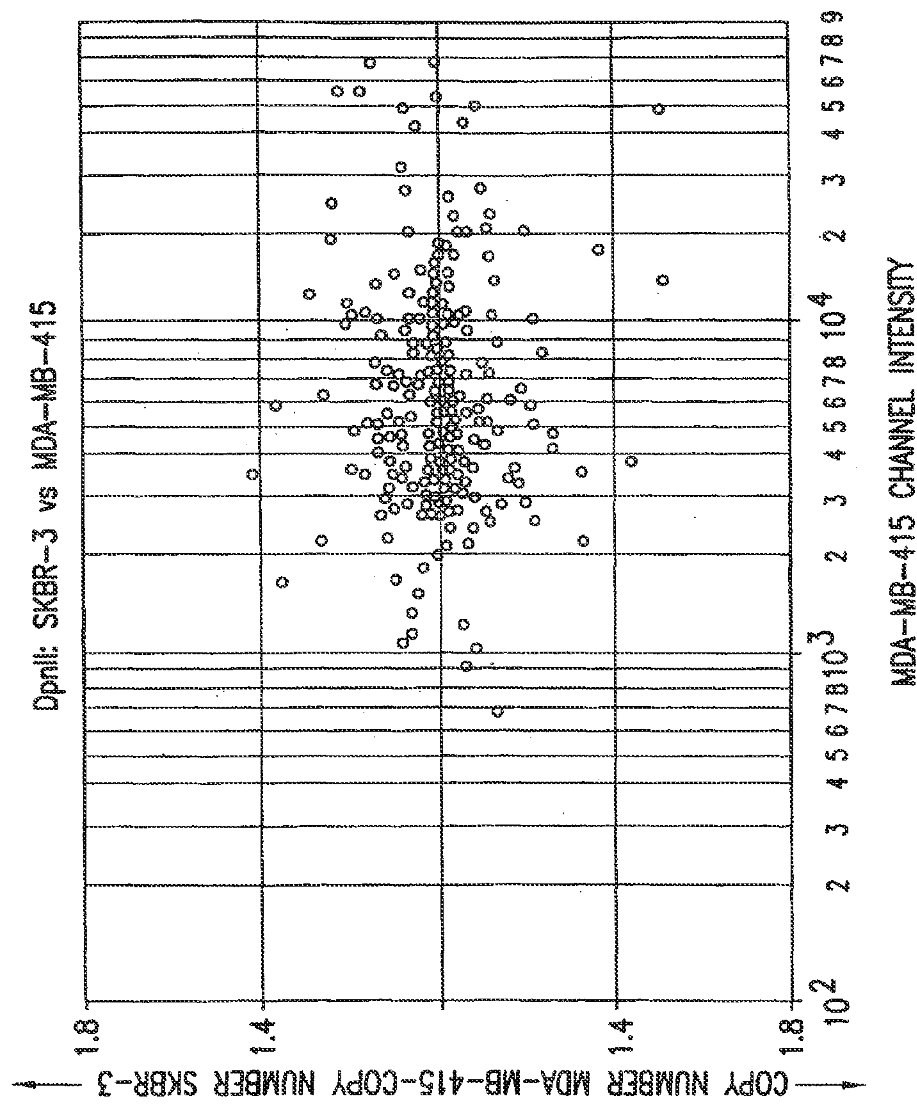

FIGS. 11 A-C show the comparison of hybridizations of BglII representations to that of DpnII representations.

5. DETAILED DESCRIPTION OF THE INVENTION

The present invention provides for the use of simple and compound representations of DNA in microarray technology. Representations are used to obtain a reproducible sampling of the genome that has reduced complexity. A representational protocol initiates with restriction endonuclease cleavages followed by ligation of oligonucleotides to the cleaved DNA. Ultimately, these oligonucleotides are used for a gene amplification protocol such as PCR. The resulting representation can be advantageously applied to microarray technology as both the arrayed probe and hybridized sample.

Other protocols to produce a sampling of the genome of reduced complexity exist, but are not readily adaptable to microarray technology. The two most common methods are whole genome amplification (Telenius et al., 1992, *Genomics* 13:718-25; Xu et al., 1993, *Hum Reprod.* 8:2206-10; Kristjansson et al., 1994, *Nat Genet* 6:19-23; Sun et al., 1995, *Nucleic Acids Res* 23:3034-40; Xiao et al., 1996, *Cytogenet Cell Genet* 75:57-62) and Inter ALU PCR (Cotter et al., 1991,

*Genomics,* 9(3):473-80; Cotter et al., 1990, *Genomics*) 7(2): 257-63). Both of these methods have distinct disadvantages.

Whole genome amplification utilizes random primers for PCR amplification. Due to the use of random primers a random sampling of the genome results. More seriously, the random priming creates an enormous variability from PCR reaction to PCR reaction, due to the variable thermal stability of primers to template, resulting in variability in sampling that is hard to control or standardize.

Inter ALU PCR utilizes alu consensus primers to amplify the unique sequences between alu sequences. Only those fragments between alu sequences and small enough to be amplified by PCR are present in the Inter ALU samplings. Like the previously described method, the disadvantage of this method is that the sampling is highly dependent on PCR conditions, especially temperature. Due to the fact that the primers for amplification are hybridizing to endogenous sequences, any mismatch between the primer and the recognition site in the alu sequence would cause a change in the representation. Any temperature fluctuation during amplification could create markedly different representations from the same sample if produced at different times. If this type of representation were used for microarray experiments, comparison from experiment to experiment would be difficult. These variations caused by inefficient amplification due to mismatch would make the production of a microarray based on this technique difficult if not impossible.

5.1. Representations

It is an object of the present invention to provide for the use of representations of DNA in microarray technologies. Any such use is within the scope of the present invention and several non-limiting examples are described below.

A representation of DNA is a sampling of DNA, for example, the genome, produced by a restriction endonuclease digestion of genomic or other DNA, followed by linkage of adaptors and then amplification with primers complementary to the adaptors (Lucito et al., 1998, *Proc. Natl. Acad. Sci. USA* 95:4487-4492, incorporated herein by reference). Generally, only fragments in the size range of 200-1200 bp amplify well, so the representation is a subset of the genome.

Representations can be made from very small amounts of starting material (e.g., from 5 ng of DNA), and are very reproducible. The reproducibility of representations has been demonstrated in several publications (Lisitsyn et al., 1995, *Proc. Natl. Acad. Sci. USA* 92:151; and Lucito et al., 1998, *Proc. Natl. Acad. Sci. USA* 95:4487-4492, both of which are incorporated herein by reference).

Any use of a simple or compound representation as a source for the probe attached to a chip, or as the sample hybridized to the chip, or as DNA from which a probe to be hybridized to an array is derived, is within the scope of the invention. Arrays comprising probes derived from a representation by any method, for example by using the representation as a template for nucleic acid synthesis (e.g., nick translation, random primer reaction, transcription of RNA from represented DNA, oligonucleotide synthesis), or by manipulating the representation (e.g., size fractionation of the representation, gel purified fragments from the representation to the array) are also within the scope of the invention. Several applications of representations to DNA microarray technology are described below.

It is preferable that the one or more represented biological samples, and at least a fraction of the DNA comprising the microarray be from the same species. In a particular embodiment, the one or more samples are from a human, and at least a portion of the DNA on the microarray is human in origin. DNA from any species may be utilized according to the invention, including mammalian species (including but not limited to pig, mouse, rat, primate (e.g., human), dog and cat), species of fish, species of reptiles, species of plants and species of microorganisms.

5.2. Representation Hybridized to a Non-Represented Simple or Compound Probe Array In one embodiment, a representation of the DNA from one or more biological samples is hybridized to a microarray that is comprised of elements not from a representation. The microarray can be a simple or a compound array. In a particular embodiment, a representation of the DNA from one or more biological samples is hybridized to a compound probe array comprised of, for example, DNA from a megacloning vector such as a BAC, YAC, PAC, P1, or cosmid. In another embodiment, the DNA in the array derives from expressed sequences such as may be obtained from cDNAs or expression sequence tags (ESTs). The DNA in the array, in these embodiments, is not from a representation. In a particular embodiment, the one or more samples hybridized to the microarray are from a human, and the microarray is comprised of DNA from one or more megacloning vectors that contain human DNA inserts. The represented samples may derive from any DNA, e.g., cDNAs or genomic DNAs, and may be high or low complexity representations. In a further embodiment, two represented samples are used, and the samples are differentially labeled so that hybridization of each sample can be individually quantitated and compared to the other sample. Differential labeling can be done with two different fluorescent indicators, e.g., Cy5-dCTP, fluorescein-dCTP, or lissamine-5-dCTP. Differential labeling and the hybridization of so labeled DNAs to microarrays are known to those of skill in the art (Schena et al., 1995, *Science* 270: 467-470; Schena et al., 1996, *Proc. Natl. Acad. Sci. USA* 93:10614-19; Schena et al., 1996, *BioEssays* 18(5):427-31; Shalon et al., 1996, *Genome Research* 6:639-645, each of which is incorporated herein by reference).

This embodiment is useful for detecting variations in gene copy number. For example, representations of genomic DNA taken from a normal sample and genomic DNA taken from a sample of a tumor biopsy from a human can be differentially labeled and hybridized to a microarray fabricated with a BAC library spanning a significant portion of the human genome. Fixed at each address of the microarray is DNA from a single, different member of the BAC library. The hybridization signal from the tumor sample can be detected and compared to that of the normal sample. The signals at most of the addresses should be similar, but an address where, for example, the tumor sample has greater fluorescence, indicates that there has been an amplification in the tumor cell genome of the sequences corresponding to the BAC insert DNA at that address. This embodiment can also be useful for detecting variations in levels of gene expression when the represented sample derives from cDNA. This embodiment can also be used to assess the reproducibility of representations by comparing hybridization patterns of different representations from the same sample. Similar or identical patterns of hybridization indicate that the representations are reproducible.

5.3. Samples Hybridized to a Represented Compound Probe Array

In a second embodiment, both the compound probe array DNA and the hybridized sample DNA are from representations. The difference from the embodiment described in section 5.2 is that the microarray is fabricated with compound probes derived from a representation. A represented compound array has DNA sequences from more than one fragment of the representation at each address. The decreased complexity of both the array and sample DNAs allows for favorable hybridization kinetics and improved detection. Preferably, the sample and microarray DNA are identically represented, i.e., cut with the same restriction enzyme, ligated to the same adaptors, and amplified via, for example, the polymerase chain reaction. This embodiment can also be used to assess the reproducibility of representations by comparing hybridization patterns of different representations from the same sample. Similar or identical patterns of hybridization indicate that the representations are reproducible.

One technique which can be used whenever the DNA to be fixed to the microarray is from a megacloning vector is representational difference analysis (RDA). (U.S. Pat. No. 5,436,142, Lisitsyn et al., 1993, *Science* 259:946-951) RDA is a subtractive DNA hybridization technique that is used to remove vector specific sequences, leaving substantially only the insert DNA. RDA can also be used to remove any other unwanted DNA sequences from the DNA to be fixed to the array, or the sample DNA. Such sequences can include repetitive DNA sequences.

In another embodiment, the compound probe array DNA is from a representation, and the hybridized sample DNA is any DNA, whether from a representation or not.

5.4. Samples Hybridized to a Represented Simple Probe Array

In another embodiment, a simple probe array made from a representation is hybridized to a sample comprising DNA, whether from a representation or not.

In yet another embodiment, the sample DNA hybridized to the microarray is a representation of DNA, e.g., genomic DNA, and the microarray is a simple probe array fabricated with a representation of DNA. A represented simple probe array has DNA from only one fragment of a representation at each address. Thus, each element of the array comprises many copies of a single DNA molecule derived from a representation of genomic DNA.

The arrayed probes of any array may, if so desired, be mapped to any known library of genomic DNA. For example, the method of orthogonal partition hybridization can be used to map DNA libraries derived from genomic DNA or representations of genomic DNA to inserts of megacloning vector libraries. Libraries of probes from representations of the total genome, which can be used later for arraying, can be mapped. The probe library could be converted into 96 well dishes, and the collection maintained by PCR and manipulated robotically. The map positions of most of the probes can be determined after arraying, and records kept electronically. Those probes that cannot be mapped to the library of genomic DNA can later be mapped either as needed or as new mapping tools become available.

Arrays of simple DNA probes can be mapped, for example, by hybridization to orthogonal partitions of libraries of megacloning vectors. This can be illustrated by the following, non-limiting example: the assignment of arrayed probes to a positionally mapped megaYAC library of about 10,000 elements. Although this example is oriented towards YACs, because an ordered collection exists, the same principles can be applied to mapping arrays of simple probes to other ordered collections of vectors.

A partition is the division of a set into subsets, such that every element of the set is in one and only one subset. Two partitions are called orthogonal if the intersection (i.e., the common elements) of any two subsets, one from each partition, contains no more than one element of the original set. If the members of the original set are arbitrarily laid out as a square, it is easy to see that there are always at least two mutually orthogonal, and in this case, equal partitions. These can be thought of as the partition of rows, and the partition of columns. There is a third mutually orthogonal and equal partition, the partition of "wrapped" diagonals, which will not be utilized in this example. These partitions have the additional property that each subset from one intersects each subset from the other in exactly one element. Each subset of one partition intersects a subset from another partition at a single element, and every element is the intersection of two subsets. Applying these ideas to a YAC library of 10,000 members, we see that it is possible to make two equal and orthogonal partitions of this library, each partition having about 100 subsets of about 100 members each. Many other pairs of orthogonal partitions can be envisioned, in particular, ones with larger numbers of smaller subsets.

Hybridization with representations of subsets from two orthogonal partitions could then be performed. If a probe hybridized to two subsets, one from each partition, that probe should have sequences in common with their intersection, which would be a unique YAC, if no YACs overlapped.

Because the YACs in a large library, such as the library contemplated in this example, will overlap, and a given probe may be in two or more members of the library, probes may hybridize to more than one subset of a partition. For example, if a probe is contained in two overlapping YACs, and hence hybridized to two subsets in each partition, there will be two possible solutions, with four candidate YACs, to the hybridization pattern with two orthogonal partitions. Knowledge of the mapping assignments of the YACs should be sufficient to resolve this ambiguity. Only one pair of YACs will be neighbors.

The case for a probe contained in three overlapping YACs is only slightly more complex. There are more possible solutions to the hybridization pattern with two orthogonal partitions: 6 possible triads, picked from nine possible candidate YACs. Even these ambiguous cases can be resolved from a knowledge of the chromosomal assignment of the YACs. The odds that three YACs picked at random all derive from the same chromosome is roughly the square of the reciprocal of the number of chromosomes (1/23), or roughly 1 in 500. If there are six possible triads of YACs that may contain the probe, it is highly likely (nearly 99% odds) that only the true triad will derive from the same chromosome. The success of resolution increases, approaching completeness, when we consider the finer map assignments of the YACs. The chances that three YACs, picked at random, are all neighbors is vanishingly small.

This embodiment is useful for detection of changes in gene copy number between normal and, for example, cancer biopsy samples, as is described in section 5.2. If the elements have been mapped, as described above, positional information of the alteration of gene copy number can be gathered.

This embodiment is also useful for extension reactions performed on an array that could be used to identify single nucleotide polymorphisms as done in the minisequencing reaction (Pastinen et al., 1997, Genome Research. 7:606-614). The elements of the microarray in this case are oligonucleotides, preferably single stranded oligonucleotides, derived from and complementary to fragments present in a representation, which oligonucleotides are fixed to the surface of the solid support of the array at their 5' ends. A representation produced from a sample is then hybridized to the array. Next, the oligonucleotides are extended by incubation in the presence of polymerase, nucleotide and necessary buffer. The nucleotide that follows the oligonucleotide sequence is detected by the addition of a fluorescently tagged dideoxynucleotide (Pastinen et al., 1997, Genome Research. 7:606-614; Syvanen et al., 1990, Genomics. 8:684-692).

5.5. Compound Representations Hybridized to a Represented Simple Probe Array In another aspect of the invention, the sample DNA hybridized to the microarray is or is derived from a compound representation of DNA, and the microarray, like that described in section 5.4, is a represented simple probe array. A compound representation is the result of two or more consecutive representations. In its simplest form, a compound representation is made by making a first representation of, for example, genomic DNA, followed by the making of a second representation of the first representation. Preferably, different restriction enzymes are used for each sample representation, and the enzyme used to prepare the first sample representation and the representation immobilized on the microarray are the same.

The following non-limiting example will serve to illustrate two possible compound representations termed AcB and AsB, where A and B are any two restriction endonucleases. They derive from a first representation made by using the A restriction endonuclease. This first representation will consist of fragments that have an A restriction endonuclease site at each end, such fragments are termed AA fragments. A fragment with a B restriction endonuclease site at each end is termed a BB fragment, while fragments with an A restriction endonuclease site at one end and a B restriction endonuclease site at the other is termed an AB fragment. AcB representations consist of AB and BB fragments that derive from those AA fragments of the simple A representation that contain a B restriction endonuclease site. AsB representations consist of those AA fragments of the simple A representation that do not contain a B restriction endonuclease site.

AsB is made by making a first representation with the restriction endonuclease A, then making a second representation by cleaving the resulting AA fragments with the restriction endonuclease B and amplifying with the same primers used in the first representation. AA fragments from the first representation that have an internal B site are cut by the B restriction endonuclease and will not amplify, while those AA fragments lacking an internal B site will amplify. The final representation then consists only of those AA fragments with no internal B site.

The second representation, designated AcB, is also made from a first simple A representation, i.e., a representation made with restriction endonuclease A. AcB is made, like AsB, by making a first representation with the restriction endonuclease A, then making a second representation by cleaving the resulting AA fragments with the restriction endonuclease B. This cleavage results in three types of fragments: 1) AA fragments, i.e., those AA fragments without internal B sites, 2) AB fragments, i.e., fragments with an A site at one end and B site at the other, derived from those AA fragments with one or more internal B sites, and 3) BB fragments, derived from those AA fragments with more than one internal B site. The difference between the AcB and AsB representations is in the amplifications steps of the second representation. In the AcB representation, oligonucleotide adaptors ("B adaptors") are ligated at the B site on both the 5' and 3' ends. Then, an A adaptor is ligated to the 5' end only. This adaptor has a different, sequence than the adaptor used for the first, simple representation, and is much longer, on the order of 40 nucleotides. After ligation, and removal of unligated adaptors, the ability of these molecules to extend from the 3' end is removed by dideoxy extension. Finally, primers to the A and B adaptors are added and the product is exponentially amplified by PCR using a polymerase without 3' exonuclease activity. Only AB and BB fragments are strongly favored to amplify.

The protocol for AcB may seem more complex than needed. The reason for adding the A adaptor to the 5' end only is to disable exponential amplification from strands that have A at both ends. Even with this step, there will be some AA fragments that reanneal during the polymerase chain reaction step, fill-in at their 3' ends during the chain elongation step, and subsequently amplify from the A oligonucleotide primer, thereby poisoning the representation. Hence, two more features are added. The new A adaptor is long (40 nucleotides or longer). Those AA molecules that do form, and become adapted at their 5' and 3' ends by self priming, will amplify very poorly because the length of the adaptor will create thermally stable "pan handles", as described below. Finally, the 3' ends of all A sites are blocked by dideoxy extension to reduce the possibility of self priming after reannealing, and the subsequent formation of amplifiable AA fragments.

AcB and AsB representations are useful for detecting internal polymorphic restriction endonuclease sites and for detecting heterozygous and homozygous states with respect to those polymorphic sites. When a simple DNA probe chip made with a simple A representation (i.e., the first representation of the AcB or AsB compound representations) is hybridized with differentially labeled AcB (for this example, a red label) and AsB (for this example, a green label) representations, both homozygous and heterozygous states are readily detected: high red ratios indicate both alleles have B sites; high green ratios indicate both alleles do not have B sites; and ratios near equality (yellow) indicate the heterozygous state. In a preferred embodiment, the second restriction endonuclease, i.e., the B restriction endonuclease is one that recognizes CpG, such as TaqI. Such restriction endonucleases are especially useful since the sequence CpG is especially polymorphic.

5.6. Preparation of Representations

Briefly, representations are generated by restriction endonuclease digestion of DNA, followed by linkage of adaptors and then amplification with primers complementary to the adaptors. The DNA may be from any source. The method is adaptable to any genome. It is often advantageous to isolate DNA contemporaneously from both normal and diseased cells, for example, from normal and cancerous tissue, preferably from the same individual. Parallel processing of the samples allows for more accurate comparisons of the representations generated from the two different sources of cells.

The DNA is isolated by any convenient means, and then substantially completely digested by any means, such as the use of a restriction enzyme endonuclease, which results in cutting at predetermined sequences.

The complexity of the representation can be shaped in several ways. High complexity representations (HCRs) are obtained by cleaving the DNA of interest with a relatively frequent cutting restriction enzyme, such as DpnII. This results in a majority of the fragments being between 200-1200 bp, and therefore amplifiable. Representations derived from DpnII digests have about 70% of the complexity of the entire genome, i.e., 70% of the genome is present in such a representation.

Low complexity representations (LCRs) are obtained by cleaving the DNA of interest with a relatively infrequent cutting restriction enzyme, such as BamHI or BglII, resulting in a minority of the fragments being between 200-1200 bp. Representations derived from BamHI or BglII digests have about 2%, the complexity of the entire genome.

A restriction enzyme which is inhibited by methylation of the DNA can be selected for the digestion step. The use of such an enzyme can reveal differences in methylation between compared samples. This can be useful because, for example, it has been suggested that there are differences in methylation between normal cells and some cancerous cells.

Complexity of the representation can also be shaped by the adaptors used for amplification. Because the same adaptors are used at both ends of the cleaved fragments, the single strands form panhandles (Lukyanov et al., 1995, *Anal. Biochem.* 229:198-202, incorporated herein by reference). This inhibits amplification by PCR, because panhandle formation competes with PCR primer annealing, a necessary step for amplification. Shorter fragments are preferentially inhibited due to the close proximity of the adaptors resulting effectively in a higher local concentration of the 5' and 3' adaptors linked to the ends of such fragments, as compared with longer fragments. Adaptors that form panhandles of 29 nucleotides allow for amplification of fragments in the size range of 200-1200 bp. Shorter adaptors that form panhandles of 24 nucleotides release some of the inhibition of the smaller fragments, resulting in the favoring of smaller PCR amplification products, and therefore, a representation of altered complexity.

The DNA may be from any source. Sources from which representations can be made include, but are not limited to, tumor biopsy samples, including breast cancer and prostate cancer biopsies, normal tissue samples, tumor cell lines, normal cell lines, cells stored as fixed specimens, autopsy samples, forensic samples, paleo-DNA samples, microdissected tissue samples, isolated nuclei, and fractionated cell or tissue samples.

The degree of complexity of the representation generated is related to the frequency of cutting, specifically, more frequent cutting enzymes will result in higher complexity representations. Thus, representations of the desired complexity can be produced by the selection of the appropriate enzyme. The selection can be made with the guidance of the art, including readily available information on the frequency of cutting of various enzymes and the average fragment lengths generated by said enzymes (Bishop et al., 1983, A Model For Restriction Fragment Length Distributions, *Am. J. Hum. Genet.* 35:795-815). To prepare representations from highly degraded DNA it may be preferable to use restriction endonucleases that cleave with relatively greater frequency than, for example, a restriction enzyme such as DpnII.

After digestion of the DNA, the oligonucleotide adaptors are ligated to the ends of each of the strands of the DNA. The adaptor will usually be staggered at both ends, with one strand being longer than the other and therefore being single stranded over a small region at the end not ligated to the digested fragments. In the case when the restriction enzyme digestion leaves staggered ends, the adaptor will have an end complementary to the fragments' staggered ends.

The DNA is then amplified by an amplification reaction, for example, by adding primer and using the polymerase chain reaction for usually at least 15 cycles and generally not more than about 35 cycles. The primer will be complementary to the adaptor. The adaptors are then removed by restriction endonuclease digestion and separation, using any convenient means.

For purposes of comparing representations from two different sources, it is preferable that HCRs are prepared from the same amount of starting material, that the genomic DNAs are extracted in the same manner, and that PCR is performed at the same time under the same conditions in the same thermal cycler.

5.7. Preparation of Microarrays

Microarrays for use in the present invention are known in the art and consist of a surface to which probes can be specifically hybridized or bound, preferably at a known position. Each probe preferably has a different nucleic acid sequence. The position of each probe on the solid surface is preferably known. In one embodiment, the microarray is a high density array, preferably having a density of greater than about 60 different probes per 1 $cm^2$.

To manufacture a microarray DNA probes are attached to a solid support, which may be made from glass, plastic (e.g., polypropylene, nylon), polyacrylamide, nitrocellulose, or other materials, and may be porous or nonporous. A preferred method for attaching the nucleic acids to a surface is by printing on glass plates, as is described generally by Schena et al., 1995, *Science* 270:467-470. See also DeRisi et al., 1996, *Nature Genetics* 14:457-460; Shalon et al., 1996, *Genome Res.* 6:639-645; and Schena et al., 1995, *Proc. Natl. Acad. Sci. USA* 93:10539-11286.

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Light-directed spatially addressable parallel chemical synthesis, *Science* 251:767-773; Pease et al., 1994, Light-directed oligonucleotide arrays for rapid DNA sequence analysis, *Proc. Natl. Acad. Sci. USA* 91:5022-5026; Lockhart et al., 1996, Expression monitoring by hybridization to high-density oligonucleotide arrays, *Nature Biotech* 14:1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al., 1996, High-Density Oligonucleotide arrays, *Biosensors & Bioelectronics* 11:687-90). When these methods are used, oligonucleotides (e.g., 20-mers) of known sequence are synthesized directly on a surface such as a derivatized glass slide.

Other methods for making microarrays, e.g., by masking (Maskos and Southern, 1992, *Nuc. Acids Res.* 20:1679-1684), may also be used. In principal, any type of array, for example, dot blots on a nylon hybridization membrane (see Sambrook et al., Molecular Cloning—A Laboratory Manual (2nd Ed.), Vol. 1-3, Cold Spring Harbor Laboratory, Cold Spring Harbor, N.Y., 1989, which is incorporated in its entirety for all purposes), could be used, although, as will be recognized by those of skill in the art, very small arrays will be preferred because hybridization volumes will be smaller. Presynthesized probes can be attached to solid phases by methods known in the art.

5.8. Preparation of Sample Nucleotides

Sample to be hybridized to microarrays can be labeled by any means known to one of skill in the art. The sample may be from any source, including a representation, cDNA, RNA or genomic DNA. In a particular embodiment, the sample is labeled with a fluorescent probe, by, for example, random primer labeling or nick translation. When the sample is a representation, it may be labeled during the PCR step of making the representation by inclusion in the reaction of labeled nucleotides. The fluorescent label may be, for example, a lissamine-conjugated nucleotide or a fluorescein-conjugated nucleotide analog. Sample nucleotides are preferably concentrated after labeling by ultrafiltration.

In a particular embodiment, two differentially labeled samples (e.g., one labeled with lissamine, the other fluorescein) are used.

5.9. Hybridization to Microarrays

Hybridization of a representation of a sample to an array encompasses hybridization of the representation, or nucleotides derived from the representation by any method, for example by using the representation as a template for nucleic acid synthesis (e.g., nick translation, random primer reaction, transcription of RNA from represented DNA), or by manipulating the representation (e.g., size fractionation of the representation, gel purified fragments from the representation to the array).

Nucleic acid hybridization and wash conditions are chosen such that the sample DNA specifically binds or specifically hybridizes to its complementary DNA of the array, preferably to a specific array site, wherein its complementary DNA is located, i.e., the sample DNA hybridizes, duplexes or binds to a sequence array site with a complementary DNA probe sequence but does not substantially hybridize to a site with a non-complementary DNA sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., 1996, *Science* 274:610-614).

Arrays containing double-stranded probe DNA situated thereon are preferably subjected to denaturing conditions to render the DNA single-stranded prior to contacting with the sample DNA. Arrays containing single-stranded probe DNA (e.g., synthetic oligodeoxyribonucleic acids) need not be denatured prior to contacting with the sample DNA.

Optimal hybridization conditions will depend on the length (e.g., oligomer versus polynucleotide greater than 200 bases) and type (e.g., RNA, DNA) of probe and sample nucleic acids. General parameters for specific (i.e., stringent) hybridization conditions for nucleic acids are described in Sambrook et al., supra, and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1×SSC plus 0.2% SDS) (Shena et al., 1996, *Proc. Natl. Acad. Sci. USA* 93:10614). Useful hybridization conditions are also provided in, e.g., Tijessen, 1993, Hybridization With Nucleic Acid Probes, Elsevier Science Publishers B. V. and Kricka, 1992, Nonisotopic DNA Probe Techniques, Academic Press San Diego, Calif.

5.10. Detection of Hybridization

Hybridization to the array may be detected by any method known to those of skill in the art. In a particular embodiment, the hybridization of fluorescently labeled sample nucleotides is detected by laser scanner. When two different fluorescent labels are used, the scanner is preferably one that is able to detect fluorescence of more than one wavelength, the wavelengths corresponding to that of each fluorescent label, preferably simultaneously or nearly simultaneously.

5.11. Generation of High Complexity Representations

Briefly, High Complexity Representations (HCRs), are generated by restriction endonuclease digestion of DNA, followed by linkage of adaptors and then amplification with primers complementary to the adaptors. The DNA may be from any source. The method is adaptable to any genome. It is often advantageous to isolate DNA contemporaneously from both normal and diseased cells, for example, from normal and cancerous tissue, preferably from the same individual. Parallel processing of the samples allows for more accurate comparisons of the two HCRs generated from the two different sources of cells.

The DNA is isolated by any convenient means, and then substantially completely digested by any means, such as the use of a restriction enzyme endonuclease, which results in frequent cutting at predetermined sequences.

In one embodiment, a "relatively frequent cutting restriction endonuclease" is used. As used herein, the term "relatively frequent cutting restriction endonuclease" is intended to mean a restriction endonuclease which has a consensus sequence of four or fewer nucleotides, and may provide for blunt ends or staggered ends. Exemplary "relatively frequent cutting, restriction endonucleases" include, but are not limited to DpnII, Tsp509I, MboI, Sau3A1, MaeII, MspI, HpaII, BfaI, HinPI, Csp61, TaqI, MseI, AluI, BstUI, DpnI, HaeIII, RsaI, HnaI, and NlaIII.

In an alternative embodiment, at least two restriction enzymes are used simultaneously or sequentially to cut DNA with the desired frequency. The enzyme combination used should be chosen such that at least about 50% of the fragments produced by the digestion will be between 100 and 1000 nucleotides in length. It is within the skill in the art to select such combinations. Bishop et al., 1983, *Am. J. Hum. Genet.* 35:795-815, incorporated by reference herein).

A restriction enzyme which is inhibited by methylation of the DNA can be selected for the digestion step. The use of such an enzyme can reveal differences in methylation between compared samples. This can be useful because, for example, it has been suggested that there are differences in methylation between normal cells and some cancerous cells.

As detailed above, the degree of complexity of a representation is related to the frequency of cutting, specifically, more frequent cutting enzymes will result in higher complexity representations. Thus, representations of the desired complexity can be produced by the selection of the appropriate enzyme. To prepare HCRs from highly degraded DNA it may be preferable to use restriction endonucleases that cleave with relatively greater frequency than, for example, a restriction enzyme such as DpnII.

After digestion of the DNA, the oligonucleotide adaptors are ligated to the ends of each of the strands of the DNA. The adaptor will usually be staggered at both ends, with one strand being longer than the other and therefore being single stranded over a small region at the end not ligated to the digested fragments. In the case when the restriction enzyme digestion leaves staggered ends, the adaptor will have an end complementary to the fragments' staggered ends.

The DNA is then amplified by an amplification reaction, for example, by adding primer and using the polymerase chain reaction for usually at least 15 cycles and generally not more than about 35 cycles. The primer will be complementary to the adaptor. The adaptors are then removed by restriction endonuclease digestion and separation, using any convenient means.

For purposes of comparing HCRs from two different sources, it is preferable that HCRs are prepared from the same amount of starting material, that the genomic DNAs are extracted in the same manner, and that PCR is performed at the same time under the same conditions in the same thermal cycler.

5.12. Uses of High Complexity Representations

HCR's are useful for, among other things, determining gene copy number, deletion mapping, loss-of-heterozygosity (LOH) and comparative genomic hybridization (CGH). HCR's are also useful for microarrays, as described above. HCRs also are a generally useful means of "immortalizing" and archiving DNA for later analysis.

5.12.1. Archiving of DNA

HCRs of from the DNA of nonrenewable sources can be produced and stored, creating an archivable representation of the DNA from the original source. Further analysis can then be performed on the HCR instead of on the limited amount of original material.

5.12.2. HCRs From Stored Samples

HCRs can be prepared from normal and tumor tissue stored as fixed, paraffin embedded, archived biopsies, and this would greatly extend the utility of such samples. As compared with fresh samples, more rounds of PCR are usually required to obtain workable amounts of DNA. The amplified DNA from stored samples usually has a lower size distribution than HCRs prepared from DNA extracted from fresh sources. HCRs prepared from paired stored samples are similar to each other, which suggest that the method has utility.

5.12.3. Determination of Loss or Amplification of Genes by Measurement of Gene Copy Number Genomes often contain either extra copies of sequences due to gene amplification, or missing sequence when genes are deleted, which is known as loss of heterozygosity when one allele of a gene is lost, or loss of homozygosity when both alleles are lost. Comparison of Southern blots of HCRs from diseased cells and normal cells can reveal whether the gene corresponding to the probe (for example a probe for a tumor suppressor of oncogene) is amplified or missing in the diseased cells relative to normal cells.

Some variability in the content of HCRs will arise due to polymorphism. For example, if a given sequence in an individual is contained on a bi-allelic DpnII fragment, occurring on a large and small fragment, and the small fragment is lost in the tumor due to loss of heterozygosity, the HCR from tumor may appear to be missing the sequence in question because: 1) the large fragment will not be efficiently amplified by PCR, and will not be represented in the library, and 2) the small fragment is not present in the starting material, due to LOH. This can be used in a rapid method for loss of heterozygosity analysis if a sufficient number of such polymorphic sequences were known.

5.12.4. Comparative Genomic Hybridization with HCRS

Comparative genome hybridization (CGH) is a powerful tool for analyzing the global genomic changes in tumors. (Thomspon et al., 1993, *J. Cell. Biochem. Suppl.* 17G:139-143, Kallioniemi et al., 1993, *Semin. Cancer Biol.* 4(1):41-46) In CGH, DNA from a test sample is labeled and mixed with normal DNA that is labeled with a different fluorophore. This probe mixture is hybridized to a normal metaphase spread or other reference standard. Since the entire fluorescently labeled genome of the test sample is used to stain normal metaphase chromosomes, the intensity of the fluorescence at each location along the normal chromosomes is proportional to the copy number of gene sequences that bind there. The resulting fluorescence ratios of hybridized test DNA to normal DNA is measured. One can observe the gains and losses of whole chromosomes or insertions and deletions on a specific chromosome.

CGH can be performed with HCRs by fluorescently labeling the HCR and using it in a CGH protocol.

6. EXAMPLES 6.1. Generation of Representations

Materials

Restriction endonucleases as well as T4 ligase were supplied by New England Biolabs, Inc. Ampli Tag was supplied by Perkin Elmer Inc. Oligo adaptors RBg124 (5'_AGCACT CTCCAGCCTCTCACCGCA-3') and RBgl12 (5'-GATCT-GCGGTGA-3') were synthesized by BioSynthesis. dNTPs were supplied by Pharmacia. Cell lines used were obtained through ATCC, grown in culture and DNA from them isolated.

Production of Representations 5-10 ng of genomic DNA was digested by the desired restriction endonuclease (DpnII to produce the High Complexity Representation and Bg1II to produce the Low Complexity Representation) as suggested by the supplier. The digest was purified by phenol extracting and precipitation. The digested DNA was ligated to adaptors RBgl24 and RBg112. The ligating mixture contained the digested genomic DNA, 1× reaction buffer (from the supplier), 444 pmoles of each adaptor and water to bring the volume to 30 ul. The reaction was placed at 55° C. and the temperature slowly decreased to 15° C. After the reaction mixture reached 15° C., 400 units of T4 DNA ligase was added, and the reaction mixture was incubated at 15° C. for 12-18 hrs. The ligated material was split into two PCR tubes and amplified by PCR. The PCR reaction contained the ligated material, 1X PCR buffer (335 MM Tris-HCL, pH8.8, 20 mM $MgCl_2$, 80 mM $(NH4)_2SO_4$, 50 mM beta-mercaptoethanol, 0.5 mg/ml of bovine serum albumin), 0.32 mM dNTP's, 0.6 mM RBg124 adaptor, which was then overlaid with mineral oil. The reaction was placed in a thermal cycler preheated to 72° C. and then 15 units of AmpliTaq was added to the tube. The thermal cycler was set to continue 72° C. for 5 minutes, and then repeat 20 cycles of 1 minute at 95° C., and 3 minutes at 72° C. This was followed by an additional 10 minutes at 72° C. The reaction was purified by phenol-chloroform, and then precipitation.

6.2. Analysis of the Complexity of an HCR

We first tested the reproducibility and complexity of DpnII HCRs. We analyzed 14 different HCRs, each made from 5 ng of DNA prepared from diploid nuclei separated from tumor biopsies by flow cytometry, and each amplified for 25 rounds. In our first sampling, we designed pairs of PCR primers to detect sequence tag sites (STSs). STSs are sequences known to be present in the genome, to which no particular function has been attributed. We picked STSs that were not cleaved by DpnII, and used primer pairs that amplified a single band from total genomic DNA controls. Of these, 18 of 25 pairs (72%) were able to amplify the same molecular weight fragment from each HCR, and 7 generally failed to amplify from any HCR (see FIG. 1 for representative data). Our results suggests that DpnII HCRs reproducibly contain the same elements and about 70% of the genome.

We performed a similar test with primer pairs derived from the locus encoding the PTEN tumor suppressor gene, for which locus we had the complete nucleotide sequence. In this way we were able to use primers derived from DpnII fragments of known size. DpnII fragments were chosen at random, and PCR primer pairs designed for each. 22 pairs amplified single fragments by PCR from control genomic DNAs. These pairs were tested against the panel of 14 HCRs. Table 1 lists the size of the DpnII fragments from which the probes were derived.

TABLE 1

| Fragment | Fragment Size | Present (+) or Absent (−) |
|---|---|---|
| 1 | 94 | + |
| 2 | 97 | − |
| 3 | 126 | + |
| 4 | 134 | + |
| 5 | 160 | + |
| 6 | 193 | + |
| 7 | 415 | + |
| 8 | 424 | + |
| 9 | 460 | + |
| 10 | 466 | + |
| 11 | 466 | + |
| 12 | 495 | + |
| 13 | 496 | + |
| 14 | 507 | + |
| 15 | 528 | + |
| 16 | 531 | + |
| 17 | 1040 | + |
| 18 | 1049 | + |
| 19 | 1246 | + |
| 20 | 1436 | + |
| 21 | 1760 | + |
| 22 | 3916 | − |

PTEN fragments in the HCR. Fragments have been arranged by size order starting with the smallest, in the column labeled fragment size. The fragments have been numbered as a reference in the column labeled fragment. The column labeled pres or abs details the results, whether a fragment is in the HCR for each fragment from the PTEN region. The symbol + denotes presence and − denotes absence.

20 pairs amplified the expected fragment from all HCRs, and 2 pairs failed to amplify from any. The fragments that were not in the HCR were the largest, 3916 bp, and one of the smallest, 97 bp. 16,039 bp was included in the HCRs and 4013 bp were excluded. Thus, assuming our pick of fragments was random, the HCRs contained about 75% of this region.

If DpnII cleavage is nearly complete during the preparation of an HCR, we expect that no PCR primer pairs should readily amplify from an HCR when the amplified sequence has a DpnII site. To test this, we chose 5 primer pairs from the PTEN locus that amplified a single fragment containing a single internal DpII site. All 5 pairs amplified fragments from genomic DNA controls, and none amplified detectable fragments from the 14 HCRs.

We conclude that HCRs prepared in parallel from samples processed in a similar manner are reasonably reproducible and represent about 70% of the human genome.

6.3. Measuring Gene Copy Number in HCRs

Tumor genomes often contain either extra copies of sequences due to gene amplification, or missing sequence when genes are deleted. To explore the utility of representations for measuring gene copy number, we first compared Southern blots of genomic DNA to blots of HCRs and LCRs. For this purpose, we prepared genomic DNA from tumor cell lines amplified at cyclin D1 (MDA-MB-415), or c-erB2 (BT474), or c-myc (SKBr3), or human placenta. HCRs and LCRs were made from cell line or placenta DNAs using DpnII or Bg1II, respectively. As probes we used small Bg1II fragments that we cloned from P1's containing inserts from the designated loci. The blots, shown in FIG. 2, panel A, were quantitated by phosphourimaging. To normalize for loading differences, the blots were stripped and rehybridized with a single copy sequence probe. The normalized ratios of signal from tumor and normal are tabulated in FIG. 2, panel B. The same relative copy number (tumor to normal) was determined from blots of representations as was determined from blots of genomic DNAs. This indicates that there was no significant distortion in relative copy number for these probes during the preparation of either high complexity or low complexity representations when these are prepared in parallel from similar starting materials. That is, the ratio of gene "X" in tumor to a normal standard to the ratio of gene "Y" in tumor to the same normal standard is constant for genomic, LCR and HCR DNAs.

To explore the utility of HCRs for deletion mapping, we probed blots of both genomic and HCR DNAs from tumor cell lines for deletion at the 20p11 locus. This locus was discovered initially using RDA, and subsequently found to be frequently deleted in gastrointestinal cancers. FIG. 3 illustrates that the probe hybridized to sequences in the HCRs when and only when it hybridized to sequences in the respective genomic DNA.

6.4. Production and use of HCRs From Small Samples

We tested the value of the HCRs made from limiting amounts of DNA. HCRs were prepared from aneuploid and diploid nuclei sorted from several breast cancer biopsies, and blotted for c-myc. FIG. 4, illustrates that c-myc is amplified in the HCRs made from the aneuploid nuclei of some biopsy samples. We obtained confirmation of the validity of the c-myc amplifications by demonstrating that probes adjacent to but distinct from the c-myc probes were also amplified in the same samples.

6.5. Measurement of Gene Copy Number in HCRs by Quantitative PCR

Samples were tested by quantitative PCR. For this purpose, the fluorescence energy resonance transfer hybridization probes and the ABI7700 sequence detector were used to compare pairs of HCR DNAs prepared from aneuploid and diploid nuclei derived from sorted primary tumor biopsies. Probes from several genomic regions (FHIT, p16 and c-erB2) were used to determine copy number in several HCRs. The data from the ABI7700 sequence detector was analyzed with MS Excel to produce graphs where the X axis represents the cycle number during the reaction and the Y axis denotes the fluorescence produced. The results indicate that no difference in copy number were detected by probes from an uninvolved region on chromosome 3. The graphed curve for the aneuploid HCR amplified for c-erB2 arises 4 cycles sooner than does the curve for the paired diploid HCR, indicating a higher copy number for c-erB2 of about 2 exp4 (16) fold in this sample. The graphed curve for the aneuploid HCR deleted for p16 arises 4 cycles later than the paired diploid HCR, again a 16 fold difference, probably reflecting about 6% contamination of the aneuploid nucleic with diploid nuclei. One tumor/normal pair showed a shift of a single cycle for primer pairs detecting the p16 gene. This might reflect loss of a single allele in the tumor.

6.6. Detection of Loss of Heterozygosity in HCRs

Loss of heterozygosity (LOH) is a common lesion found in cancer cells, and may be indicative of genomic instability or the loss of function of a specific tumor suppressor gene. The detection of LOH is often obscured by the presence of normal stroma, and hence we tested whether HCRs prepared from minute amounts of samples highly enriched for tumor nuclei could be used for LOH analysis. PCR primers that amplify microsatellites and detect fragment length polymorphisms are frequently used for LOH mapping, and we chose to examine a primer pair that amplifies a highly polymorphic tetranucleotide repeat near the p53 locus.

Preliminary experiments established that these PCR primers detected the same allele pattern in both genomic and HCR DNAs prepared from cell lines. Twelve pairs of HCRs prepared from aneuploid and diploid nuclei were next examined. LOH at this locus was clearly detected in 9 out of 10 informative pairs (see FIG. 5 for representative cases). This is greater than the reported proportion of LOH at this locus in breast cancer (60%), but may be biased for the highly aneuploid tumors which are sortable.

6.7. Comparative Genome Hybridization with HCRs

Comparative genome hybridization (CGH) is a powerful tool for analyzing the global genomic changes in tumors. (Thomspon et al., 1993, *J. Cell. Biochem. Suppl.* 17G:139-143, Kallioniemi et al., 1993, *Semin. Cancer Biol.* 4(1):41-46). The applicability of HCRs to CGH was examined. For this experiment, tumor cell lines were chosen so that direct comparison of CGH performed with genomic and HCR DNA was possible. Little difference in patterns could be discerned with the two cell lines examined, BT474 and MCF7. FIG. 6 shows the chromosomal scanning profiles obtained for two representatives chromosomes with each DNA source.

6.8. Preparation of a Microarray

In a specific exemplary embodiment, preparation of a microarray involves the steps of preparing the glass surface, preparing probes, and depositing the probes on the surface. Exemplary protocols for these steps are presented in this subsection.

Preparation of Poly-l-lysine Slides

Use 30 slide racks in 350 mL glass dishes.

1. Dissolve 50 g of NaOH pellets into 150 ml $ddH_2O$
2. Add 200 ml of 95% EtOH, stir until completely mixed
3. If solution remains cloudy, add ddH2O until clear
4. Pour solution into glass slide box.
5. Drop in 30 slides in a metal rack. (Gold Seal slides, Cat. 3010)
6. Let soak on an orbital shaker for at least two hours
7. Rinse slides by transferring rack to slide dish filled with $ddH_2O$
8. Repeat $ddh_2O$ rinses×3. It's important to remove all traces of the NaOH-ethanol.
9. Prepare Poly-l-lysine solution: Use Sigma Poly-1-lysine solution. Cat. No. 8920
10. Add 70 mL poly-l-lysine to 280 ml of water
11. Transfer slides to lysine solution and let soak for 1 hour.
12. Remove excess liquid from slides by spinning the rack of slides on microtiter plate carriers at 500 rpm.
13. Dry slides at 40 degrees C. for 5 minutes in a vacuum oven.
14. Store slides in a closed box for at least two weeks prior to use.
15. Before printing arrays, check a sample slide to make sure it's hydrophobic (water should bead off it) but the lysine coating is not turning opaque.

Arraying

1. Transfer PCR reactions to 96-well V-bottom tissue culture plates (Costar). Add 1/10 vol. 3M sodium acetate (pH 5.2) and equal volume isopropanol. Store at −20 C for a few hours.
2. Centrifuge in Sorvall at 3500 RPM for 45 min. Rinse with 70% EtOH, centrifuge again and dry.
3. Resuspend DNA in 12 ul 3×SSC for a few hours and transfer to flexible U-bottom printing plates.
4. Spot DNA onto poly-l-lysine slides with an arrayer.

Post Processing

1. Rehydrate arrays by suspending slides over a dish of warm double distilled water. (~1 minute)
2. Snap-dry each array (DNA side up) on a 100 C hot plate for 3 seconds.
3. UV X-link DNA to the glass by using a Stratalinker set for 60 milliJoules.
4. Dissolve 5 g of succinic anhydride (Aldrich) in 315 mL of n-methyl-pyrrolidinone.
5. To this, Add 35 mL of 0.2M NaBorate pH 8.0 (made by dissolving boric acid in water and adjusting the pH with NaOH), and stir until dissolved.
6. Soak arrays in this solution for 15 minutes with shaking.
7. Transfer arrays to 95 C water bath for 2 minutes
8. Quickly transfer arrays to 95% EtOH for 1 minute.
9. Remove excess liquid from slides by spinning the lack of slides on microtiter plate carriers at 500 rpm.
10. Arrays can be used immediately 6.9. Labeling of Sample and Hybridization to a Microarray 2.5 μg each of two samples to be hybridized to a microarray are random primer labeled using Klenow polymerase (Amersham), one with a lissamine-conjugated nucleotide analog (DuPone NEN) and the other with a fluorescein-conjugated nucleotide analog (BMB). The two labeled samples are combined and concentrated for hybridization using an ultrafiltration device (Amicon).

The 5 μg of combined sample DNA is concentrated to 7.5 μl of TE buffer, denatured in boiling water and snap-cooled on ice. Concentrated hybridization solution is added to a final concentration of 5×SSC/0.01% SDS. The entire 10 μl of labeled sample DNA is transferred to the microarray surface, covered with a coverslip, placed in a humidity chamber and incubated in a 60 C water bath for 12 hours. The humidity is kept at 100% by the addition of 2 μl of water in a corner of the chamber. The slide is then rinsed in 5×SSC/0.1% SDS for 5 minutes and then in 0.2×SSC/0.1% SDS for 5 minutes. All rinses are at room temperature. The array is dried, and a drop of antifade (Molecular Probes) applied to the array under a coverslip.

6.10. Detection of Hybridization

A laser scanner is used to detect the two-color fluorescence hybridization signals from 1.8-cm×1.8-cm arrays at 20-μm resolution. The glass substrate slide is mounted on a computer-controlled, two-axis translation stage (PM-500, Newport, Irvine, Calif.) that scans the array over an upward-facing microscope objective (20×, 0.75 NA Fluor, Nikon, Melville, N.Y.) in a bi-directional raster pattern. A water-cooled Argon/Krypton laser (Innova 70 Spectrum, Coherent, Palo Alto, Calif.), operated in multiline mode, allows for simultaneous specimen illumination at 488.0 nm and 568.2 nm. These two lines are isolated by a 488/568 dual-band excitation filter (Chroma Technology, Brattleboro, Vt.). An epifluorescence configuration with a dual-band 488/568 primary beam splitter (Chroma) excited both fluorophores simultaneously and directed fluorescence emissions toward the tow-channel detector. Emissions are split by a secondary dichroic mirror with a 565 transition wavelength onto two multialkali cathode photomultiplier tubes (PMT; R928, Hamamatsu, Bridgewater, N.J.), one with an HQ535/50 bandpass barrier filter and the other with a D630/60 band-pass barrier filter (Chroma). Preamplified PMT signals are read into a personal computer using a 12-bit analog-to-digital conversion board (RTI-834, Analog Devices, Norwood, Mass.), displayed in a graphics window, and stored to disk for further rendering and analysis. The back aperture of the 20× objective is deliberately underfilled by the illuminating laser beam to produce a large-diameter illuminating spot at the specimen (5-μm to 10-μm half-width). Stage scanning velocity is 100 mm/sec, and PMT signals are digitized at 100 μsec intervals. Two successive readings are summed for each pixel, such that pixel spacing in the final image is 20 μm. Beam power at the specimen is −5 mW for each of the two lines.

The scanned image is despeckled using a graphics program (Hijaak Graphics Suite) and then analyzed using a custom image gridding program that creates a spreadsheet of the average red and green hybridization intensities for each spot. The red and green hybridization intensities are corrected for optical cross talk between the fluorescein and lissamine channels, using experimentally determined coefficients.

6.11. Random Probes, with Represented Samples of Human Genomic DNA

In the experiments of this example arrays are made with random probes (with an average length of 1 kbp) taken from the human genome. For this example we assume that a chip of 100,000 elements can be made. We choose this number for illustrative purposes.

These chips are hybridized with DNA derived from two human samples that are prepared from a tumor and from the normal cells of the same patient.

The arrays are hybridized under the conditions described in the literature (Schena et al., 1995, *Science* 270:467-70; Schena et al., 1996, *Proc Natl Acad Sci USA* 93:10614-9; Schena, 1996, *Bioessays* 18:427-31; Shaloh et al., 1996, *Genome Res* 6:639-45). Variations in these conditions can be tested to optimize the ratio of signal to noise in the hybridization, as will be discussed in detail below.

In the first experiment, total human genomic DNA is used as samples. One sample (tumor) is labeled with a fluorescent dye having a certain emission wavelength and the other labeled with a fluorescent dye having a distinguishable emission spectra. We speak of these dyes as reading in the "green" and "red" channels, respectively. The labeling follows procedures that are available in the literature (Schena et al., 1995, *Science* 270:467-70; Schena et al., 1996, *Proc Natl Acad Sci USA* 93:10614-9; Schena, 1996, *Bioessays* 18:427-31; Shalon et al., 1996, *Genome Res* 6:639-45).

Most probes of the chip (about two thirds) do not display significant hybridization signal in either the red or green channels. This is because the complexity of the human genome is so great that very little hybridization to the single copy probes on the chip occurs. (About two thirds of the human genome are single copy sequences.) About one third of probes light up very brightly in both channels. On identifying and sequencing a sample of these bright "yellow" probes (high green and red fluorescence), they turn out to contain repetitive sequences. (About one third of the human genome is repetitive sequences.) The strong green and red signals are due to the abundance of repetitive sequences in the genome, and hence, unlike single copy DNA, hybridization is readily observable. No significant alterations in green-red ratios are observed for any probe, and the experiment is uninformative.

In the second experiment, BglII representations of the genomic DNA are used, and prepared as previously described (Lisitsyn et al., 1993, *Science* 259:946-51). Bgl II representations have a complexity of about 2% the complexity of the entire human genome. The representations are labeled as before with distinguishable fluorescent dyes, "green" for tumor DNA from the biopsy and "red" with normal DNA from the same patient. The same arrays are hybridized with the two labeled representations.

The hybridized chips are then analysed by scanning in the red and green channels to derive information about the relative gene copy concentrations in tumor and normal DNAs. Most probes of the chip (about two thirds) do not display significant hybridization signal in either the red or green channels. We call these class A probes. Most probes are in this category because most probes are not repetitive nor share sequences with the BglII representations. Therefore, only background fluorescence is observed.

About one third of probes light up very brightly in both channels. We call these class B probes. On identifying and sequencing a sampling of these bright "yellow" probes (high green and red fluorescence), they turn out to contain repetitive sequences. The strong green and red signal is due to the abundance of repetitive sequences in both the genome and the BglII representation of the genome.

A smaller number of probes, perhaps about 2%, have nearly equal and measurably higher than background fluorescence in both the green and red channels. We call these class C probes. (The distinction between class B and class C probes is made more clear in the following example.) Upon sequencing a sampling of these probes, we find that almost all contain at least one BglII site, and many contain two. They are showing detectable hybridization because they share sequences in common to BglII representations. There will be a total of about 2,000 of such probes (2% of 100,000).

An even fewer number of probes, perhaps only 0.1% of 2%, or a total of about 2, display significantly stronger hybridization in the green channel than in the red channel. These class D probes, upon retrospective hybridization analysis of tumor and normal DNA by Southern blotting, are found to be significantly amplified in the tumor, indicating specific genetic lesions within the tumor. The estimate of 0.1% of 2% is based on the following. The amount of the genome that becomes amplified in an average tumor is about 3 megabases, or 0.1% of the genome, and the total number of probes in the array that share sequences with the represented sample of the genome is about 2%, as already stated.

These experiments illustrate two major points. The first point is that it is advantageous to reduce the nucleotide complexity of the sample to observe hybridization signal from single copy genomic sequences. According to the present invention in this example, we achieve this by making representations of the sample. The degree to which this complexity may be reduced is in part a function of the hybridization conditions and background noise, but reductions on the order of minimally ten fold and optimally about fifty fold are advantageous. The second point is that when using a represented sample, most randomly chosen probes are not very informative. Only those that share sequences with the represented sample are informative, and these are in a great minority. This can be remedied as is illustrated in the next examples.

These two major points are not necessarily essential when analysing lower complexity DNA populations, such as cDNA collections or genomic DNA from simpler organisms such as microbes, insects and some plants, wherein hybridization reactions go more to completion. For analysing cDNA populations, there are other reasons for preferring to represent samples or probes or both, as will be discussed in Example 6.19.

6.12. Culling Random Probes, Leading to More Informative Arrays

In the above example, most probes from the array were uninformative, either because they were unable to be used to detect hybridization to single copy DNA from the represented sample (class A) or because they recognized repeat sequences (class B). Only about 2000 probes (class C and D) were truly informative, indicating that no amplification (class C) or some amplification (class D) had occurred in the tumor.

It is possible to distinguish probes of class C or D from those of A or B, and to "cull" these probes to assemble a new array that is more efficient at detecting genetic differences between represented samples. One can clearly discard the class A probes, those that exhibit levels of hybridization that are not significantly above background. One can clearly distinguish also the class D probes. It is harder to demarcate the line between class B and class C probes. Both show higher-than-background and roughly equal hybridization signals in red and green channels. However, one can add an excess of unlabelled repetitive human DNA (also known as "Cot 1" DNA) to the hybridization mix to quench the hybridization signal to the probes that contain repetitive sequences, as is described in the literature (DeVries et al., 1995, in Current Protocols in Human Genetics, ed Boyle, A. L. (John Wiley and Sons, Inc., New York), sup 6, unit 4.6, pp 1-18). This unlabelled DNA serves as competitive inhibitor of the hybridization to the labeled samples. Thus any probe that shows diminished signal when excess unlabeled repetitive human DNA is used can be put into class B.

6.13. Representational Probes and Represented Samples: Detecting Amplification Although culling is useful to shape any collection of probes for the purposes of fabricating a more informative, and hence more efficient and economical, array, the protocol described in the above example is not the best way to assemble a collection of useful probes. On average, for every 100 probes tested, only two become chosen as useful for a BglII represented sample.

A more efficient way to assemble a collection of probes useful for assaying represented samples is to select probes from similarly represented DNA. This DNA can be total genomic DNA from tissues or cultured cells, or genomic DNA that has been cloned as an insert into a cloning vector, such as a BAC or YAC, or cDNAs. In this way, the majority of the probes of the collection will share sequences with the represented sample, and each probe has a higher probability of being informative. Thus culling of these probes, after field testing, becomes a more efficient process.

In the following example, we make a BglII representation of total human DNA, from any source of normal cells, and individually clone the representation. (Different restriction endonucleases, or more complex representations, or even RDA products from megacloning vectors such as YACs (Schutte et al., 1995, *Nucleic Acids Res* 23(20):4127-33) or somatic cell hybrids could be used.) These probes are then arrayed and fall into two main classes: those that detect hybridization with repetitive sequences (class B) and those that detect hybridization with only single copy sequences (classC). The culling procedure is thus very efficient. Useful arrays can be fabricated with such probes even without removal of the class B probes, as they will comprise not more than half and probably about 30% of the total, and the addresses of such probes can be determined and recorded later.

We now fabricate an array with 10,000 probes, which is a very practical number. As in the Example 6.11, the arrays are hybridized with labelled BglII representations of tumor (green) and normal (red) DNA. As in Example 6.12, an excess of unlabeled repetitive DNA is added to quench hybridization from repeat sequences.

Now, instead of two probes detecting genetic gene amplification in the tumor (as indicated by statistically aberrant high green-to-red ratios), we will observe on the order of ten probes detecting amplification (0.1% of 10,000). Thus, even though the array with representational probes has one-tenth the addresses as the array used in Example 6.11, and is commensurably cheaper both to fabricate and analyse, it is five times more informative.

6.14. Detecting Genetic Loss in Tumors

In the previous example we have illustrated the use of arrays hybridized to representations to detect gene amplification in tumors. A very similar protocol can be used to detect loss of genetic information in tumors. Such losses are often the hallmark of tumor progression, are usually indicative of genetic instability and the loss of a tumor suppressor gene, and can be used for diagnosis and prognosis of cancers. A variation in the protocol is necessary, because tumor biopsies invariably contain normal stroma, that is, normal cells such as fibroblasts, capillary endothelium, and blood cells. The DNA from these normal cells could obscure genetic loss within the tumor by common means of analysis, such as southern blotting and PCR analysis of loss-of-heterozygosity (Kerangueven et al., 1995, *Genes Chromosomes Cancer* 13 (4):291-4; Habuchi et al., 1995, *Oncogene* 19:11(8):1671-4). It is therefore necessary to separate the tumor and normal nuclei.

Many tumors can be distinguished from normal cells, most commonly by aneuploidy (a different amount of DNA per nucleus) or surface markers. Hence in many cases tumor nuclei of tumor cells from a biopsy can be separated from normal stroma by fluorescence activated sorting (Del Bino et al., 1989, *Anal Cell Pathol* 1(4):215-23; Maesawa et al., 1992, *Jpn J Cancer Res* 83(12):1253-6) into populations that are 90% free of normal nuclei. Alternately, the normal stroma of tumor biopsy specimens can be microdissected and relatively pure populations of tumor cells obtained. DNA can be prepared from as few as 5000 tumor cells or nuclei obtained by these means, and representations prepared. By comparing the tumor with normal representations in array format, as in the above example, genetic losses in the tumor can be detected.

This genetic loss can occur in two fundamental varieties. First, homozygous loss, where both copies of a gene have been lost in the tumor, will result in the absolute loss of those sequences. When those sequences encompass an element that both is present in the representation of the normal DNA and shares sequences with a probe of the array, the absence of those sequences will be detected by a high red-to-green ratio for that probe. That is, the array will detect the sequences present in the normal sample but absent in the tumor sample. We have estimated that, on average, a tumor loses about 3 megabases of sequence through homozygous loss, or about 0.1% of the genome. Thus we expect that about 10 probes from a 10,000 member array would detect loss.

Second, heterozygous loss, or LOH, can frequently be detected by an array based on representational analysis. In LOH only one of two alleles of a tumor is lost, and the explanation for the detection differs from that of homozygous loss. Individuals have genetic polymorphisms that are frequently manifest as restriction fragment length polymorphisms. Hence, sequences from one allele may be in a representation, due to being on a low molecular weight restriction endonuclease fragment, while sequences from the other allele are not. If the allele that is in a representation is the allele that is lost in the tumor, then that loss can be detected by the array, provided that sequence is shared with one of the arrayed probes. Previous estimates are that cancers lose about 15% of their genome through this mechanism. Depending on the density estimates of restriction endonuclease polymorphisms, upwards of 0.6% of the representation will be lost in the tumor, or about 60 probes per 10,000 member array.

6.15. Optimizing Hybridization Conditions

Hybridization of nucleic acid, whether it be RNA or DNA, to the DNA fragments on the array is affected by several factors including complexity, concentration, ionic strength, time, temperature, and viscosity (Wetmur et al., 1968, *Mol Biol* 31(3):349-70; Wetmur, 1976, *Annu Rev Biophys Bioeng* 5:337-61). By varying these factors we are able to optimize the hybridization conditions to allow for the highest signal with the lowest possible background.

By making a representation of the DNA sample we have already addressed the issue of complexity. In the event that the representation that we are using is still too complex to allow for favorable hybridization kinetics, we have the option of altering the representation to further decrease the complexity. One option to achieve this is to change the restriction enzyme that is being used for the production of the representation to an enzyme that cuts less frequently than the current enzyme we are using. A second option is to cleave the representation with a second restriction enzyme. However, the pitfall to doing this is that information is lost with every complexity reduction. Part of optimization entails choosing the representation that gives favorable hybridization kinetics but also yields as much information as possible.

The concentration of the sample also is an important factor that effects the rate of hybridization. The fact that we are producing representations for the hybridization puts us at an advantage as compared to many other chip techniques. We can make virtually unlimited amounts of representation for hybridization. In this way we can approach if necessary the maximum DNA concentration in solution. For example, sample concentrations of 1 ug/ul up to 8 ug/ul can be used, if necessary.

Hybridization rates have been determined to be strongly dependent on the Na ion concentration ranging up to 3.2 M. One can, for example, start with a 0.5 M Na ion concentration, and vary this concentration from 0.25M up to 1M to optimize the Na ion concentration. Time of incubation also affects the completion of the hybridization reaction. One can vary this factor up until we reach 24 hours, or more if necessary. Preferably, we use the shortest time that will give us the best signal to noise ratio.

The temperature of hybridization may also be varied. The optimum temperature for hybridization of a fragment would be 25 C below its melting temperature. We are asking for many fragments of different size and content from a representation to hybridize to their complementary probes in the microarray during the same incubation. Current protocols for hybridization use a temperature of 65 C. One can vary this temperature from, for example, 55 C to 75 C to determine the optimum temperature of hybridization for our purposes.

The rate of hybridization can be increased by the addition of neutral polymers to the solution. It is believed that the polymer excludes water from solution increasing the local concentration of nucleic acid. One can increase the rate of hybridization by the addition of a neutral polymer such as ficoll.

6.16. More Culling, Leading to More Reliable and Interpretable Array Data

As will be understood by those of skill in the art, routine optimization of the arrays can take into account following. We have observed that a small minority of probes in an array are not reliable, in that they display variable hybridization signals even from representations prepared in parallel from the same sample. We presume that even in representations made as we have described, there may be some variability in the amplification of certain elements. It is useful therefore to test arrays made from a given collection of probes with multiple independent and parallel representations made from the same samples, to mark and note those probes which exhibit this behavior. They can then be culled from the collection.

We have previously discussed culling probes (Example 6.12), wherein useful probes are retained in a collection, and useless probes are discarded. This segregation of probes was physical, and arrays were fabricated that had higher concentrations of useful probes. However, when, as in this example, a small minority of probes is found to be useless, a more economical approach is achieved by making an electronic "black list", wherein the readings for a probe is marked as "to-be-ignored".

6.17. Polymorphic Analysis

As we indicated in Example 6.14, organisms are genetically polymorphic. That means that arrays based on representations can be used to provide a signature for individuals, which might be useful in forensic identification, or be used to follow genetic crosses between individuals, for example to determine paternity.

We can prepare representations, say BglII representations, from the DNAs of one individual, labeled with green, and compared to a "standard" human BglII representation labeled in red, using a BglII representational array containing, for example, 1000 probes. We estimate that polymorphic differences will be observed for roughly one out of 60 probes, resulting in differences (high green-to-red or high red-to-green ratios) at about 15 addresses out of 1000. This provides a "digit signature" for that individual as unique as a 1000 digit number in base three (with digits of green, yellow and red) with about 15 non-yellow digits. The number of such possible signatures is in excess of 10 to the 35th power. Larger arrays, or using compound representations of samples, as described in the next example, can provide an even more astronomically unique signature. From this genetic typing, that individual can be identified from a DNA sample.

The application of this method can be applied to a child, and the child's assumed biological parents, to determine if the parentage is correct. Due to the laws of Mendelian inheritance, if parentage is correct, all "green" digits in the child's digit signature should have a green value in at least one parent. In more classical terms, the child possessing a "green allele" at an address (that is, the presence of the small fragment allele) must have inherited the same from either mother or father or both. Similarly, if the child displays a "yellow" digit for an address, then either mother or father must have a yellow digit at that address.

By comparison to different "standard" humans, this method of analysis can be further enhanced, because each comparison of different individuals will yield a different signature.

6.18. Compound Representations to Expand LOH and Polymorphic Analysis, and Enable Determination of Point Mutation Loads The simplest compound representation can be made by cleavage with a first restriction endonuclease, addition of linkers to those cleavage sites, cleavage with a second restriction endonuclease and then PCR amplification. This representation will consist of all the small fragments in the genome made by the first cleavage that do not contain restriction endonuclease sites for the second enzyme. By comparing samples made by compound representations, using representational arrays based on the first enzyme, we can thus score for polymorphic differences between samples at the second enzyme. Since the choice for the second enzyme is virtually unlimited, the same array can be used to detect many more polymorphic differences between two samples than can be detected without the use of compound representations.

Thus the use of compound representations expands the usefulness of arrays in the determination of identity (polymorphic analysis) and genetic loss in cancer (LOH analysis).

However, the use of compound representations makes possible a new use of representational arrays in cancer diagnosis. Cancers accumulate point mutations. Occasionally these point mutations destroy a restriction endonuclease site. If the site destroyed is the site of the second enzyme, the compound representation of the tumor will contain a sequence that is not present in the same compound representation from the normal DNA of that patient. If the tumor representation is labeled in green and the normal in red, "green" addresses most likely will reflect point mutation in the tumor (after correcting for gene amplification, which can be determined by comparing the simple representations). This gives the tumor a digit signature of greens. The number of green digits reflect the point mutation load in the tumor, which may have predictive and prognostic value. Moreover, the signature of a biopsied tumor can provide a marker that can be used to determine if a second tumor arising in the same patient is an independent primary tumor or a metastasis of the first.

6.19. Application of Representational Approaches to Expression Arrays

The use of arrays of cDNA probes and cDNA oligonucleotide probes to measure expression levels is well established (Schena et al., 1995, *Science* 270:467-70; Schena et al., 1996, *Proc Natl Acad Sci USA* 93:10614-9; Schena, 1996, *Bioessays* 18:427-31). In these uses, cDNAs or cRNAs from samples are prepared and analysed. The starting material from the sample is typically mRNA, and when the sample is available only in small amounts, it is problematical to perform the expression assays at all.

For this reason, it will often be desirable to prepare high complexity representations of the cDNAs prepared from limiting amounts of sample. Representations can be made in almost unlimited quantities from even small amounts of starting material, and therefore hybridized to chips at higher concentrations, thereby increasing the sensitivity and reliability of the expression assays.

In this example, it is not absolutely necessary that the probes of the array derive from the representation, for the use of high complexity representations of the sample insures that most probes will share sequences with sequences amplified in the sample representations. Nevertheless, a cDNA probe array would function more efficiently if the probes are selected to share sequences with the representations made from expressed genes.

6.20. Arrays with Compound DNA Probes or Oligonucleotide Probes Hybridized to Representations The above examples are described in relation to arrays of simple DNA probes. Each probe in the above examples comprises a single cloned sequence of DNA with a length roughly between 100 to 1000 bp (This range is not intended to define the term "simple DNA probes", it is merely an example thereof). The applications of arrays of compound probes, such as probes derived by representing YAC or BAC inserts, would not be much different. The major difference between arrays of simple probes and compound probes is that that LOH and polymorphic analysis could not be readily performed upon the latter. With arrays of compound probes gene amplification and homozygous loss could still be detected, essentially as described in Examples 6.13 and 6.14.

Another type of array can be made with oligonucleotide probes (Cho et al., 1998, *Proc Natl Acad Sci USA* 31:95(7): 3752-7; Pease et al., 1994, *Proc Natl Acad Sci USA* 91(11): 5022-6; Lipshutz et al., 1995, *Biotechniques* 19(3):442-7). There are advantages to fabricating such probes, both in terms of reproducibility, probe density, avoidance of repetitive sequences and cost (when large-scale production is desired). All the applications discussed in the above examples can be readily translated into the oligonucleotide format, provided that the oligonucleotide sequences of the array are contained in the sequences of the representations used to prepare sample. Thus they will detect elements in the representation by hybridization.

This can be achieved in the following manner. DNA probes cloned from a representation are collected and sequenced. The sequencing does not need to be complete, and may extend merely as a single read from the ends of the cloning site. This sequence information is then used to synthesize the oligonucleotides that will be used on the array.

For some applications it may be preferable to first design arrays of simple DNA probes, and then characterize the properties of the probe arrays. Afterwards, the collection of DNA probes can be sequenced and the information used to format synthetic oligonucleotide arrays.

6.21 Detecting Gene Copy Number Fluctuations in Tumor Cells by Microarray Analysis of Representations To perform this analysis, we array probes derived from a low complexity representation (LCR) of a standard human genome, and then hybridize these microarrays with LCRs of paired samples, one normal and one cancer. There are many advantages to this approach. Because LCRs have lower nucleotide complexity than total genomic DNA, we obtain a strong specific hybridization signal relative to nonspecific hybridization and noise, and are able to readily detect both amplifications and deletions in samples using short probes. Our resolution is limited only by the number of probes that can be microarrayed, and does not depend upon knowledge of the complete set of genes. Moreover, we can reliably detect allelic losses. Because the method is based on representations, samples can be prepared from microscopic amounts of tissue. The probe collection can be maintained as cultures of individual bacterial clones, and produced for printing by PCR. Finally, the methods for arraying, labeling and hybridizing are the same ones in common use for cDNA analysis.

Using two different pilot arrays of 1000 to 2000 small BglII fragments, we demonstrate that the method yields reproducible and verifiable results. We demonstrate the utility of our method for the analysis of microscopic amounts of material from a tumor biopsy, and we examine the critical parameter of nucleotide complexity. Finally, we discuss our results.

Reproducibility of Array Hybridization Data

Any measuring tool must satisfy the criterion of reproducibility. Microarray hybridization has been extensively tested, and because we use it to measure gene ratios between two samples, it is particularly robust. However, we have introduced the added element of representation during the preparation of samples. We have therefore tested the reproducibility of our measurements when independent representations are made from the same DNA source and hybridized to microarrays.

Figure 7A:
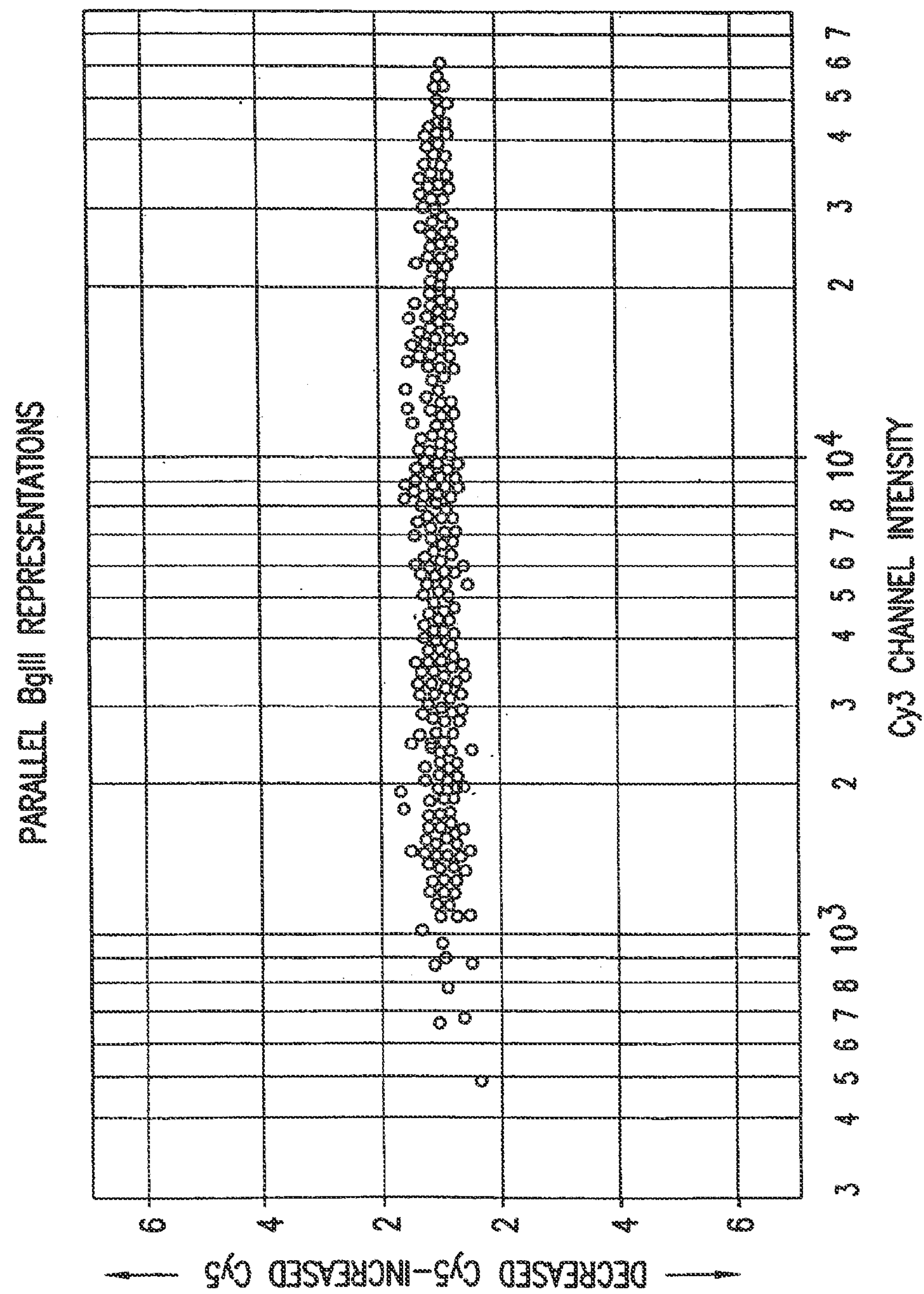
Figure 7B:
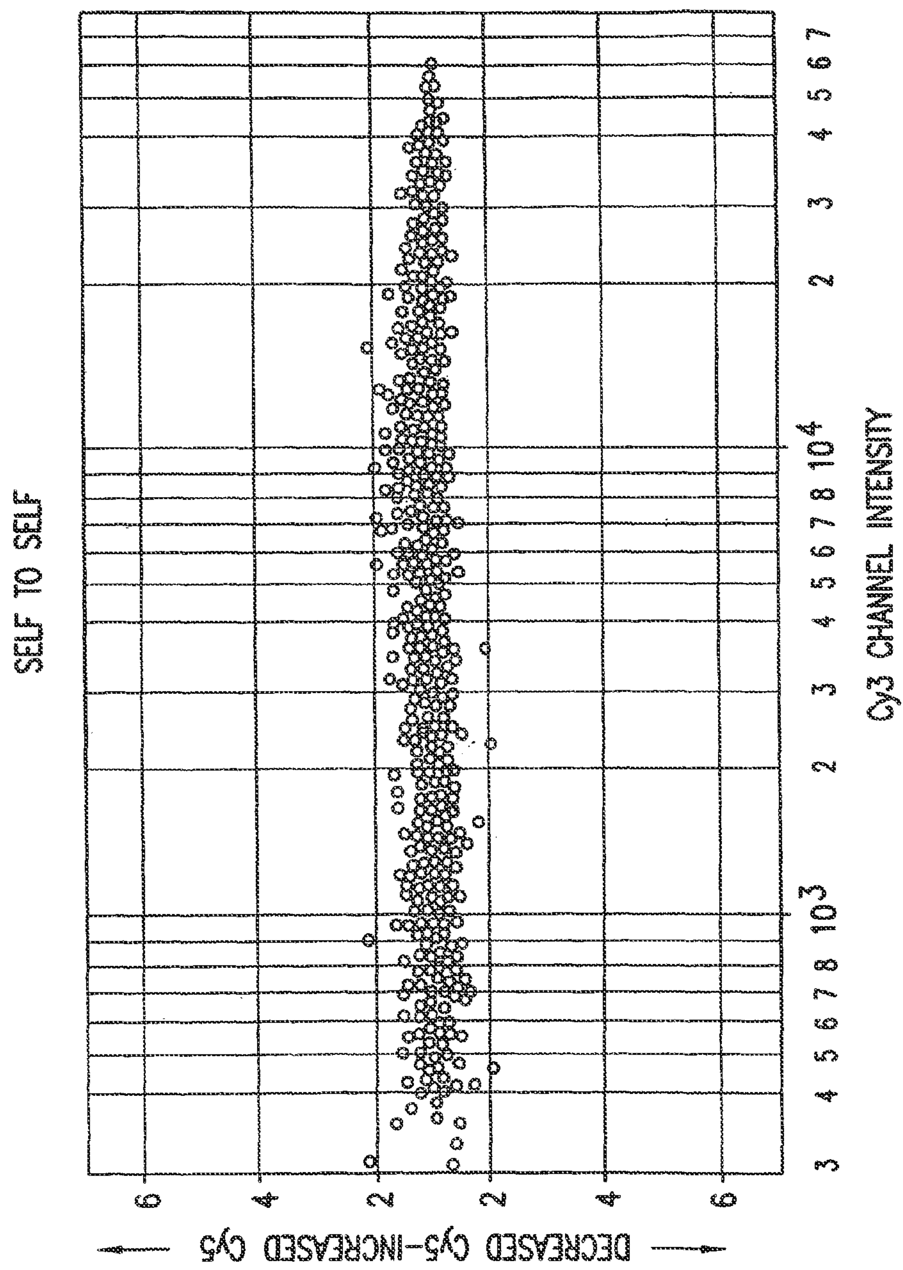
Figure 7C:
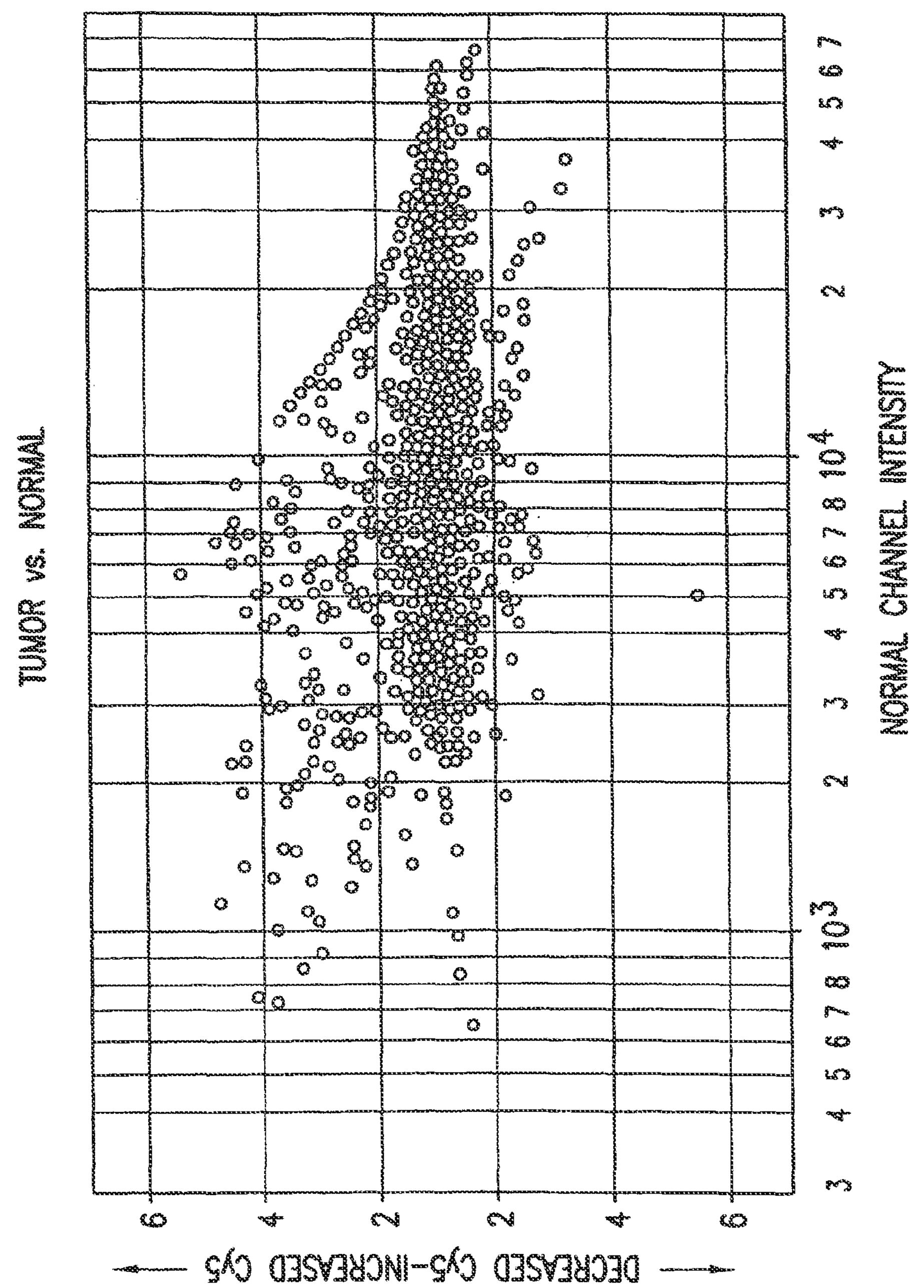

For this series of experiments, we used DNA from a human breast cancer cell line, SKBR-3, and made multiple parallel BglII representations on separate days. These were separately labeled with Cy3 or Cy5, the two fluorochromes commonly used for this purpose, and hybridized in pairs to pilot arrays. The pilot arrays contained 1658 human BglII fragments, of size range 200 to 1000 bp, printed in duplicate, for a total of 3316 features (i.e., microarray addresses). FIGS. 7A-C depict the results of microarray experiments graphed such that the intensity of one channel (usually the Cy3 channel) is the abscissa and the ratio of Cy5 to Cy3 is the ordinate. (A) BglII representations were produced separately from the same source of genomic DNA, differentially labeled and then hybridized to an array of 3316 features (1658 printed in duplicate). (B) One BglII representation was differentially labeled and then hybridized to the microarray described in panel A. (C) A breast primary tumor was separated into normal and tumor nuclei by sorting, and genomic DNA prepared. BglII representations prepared from the genomic DNA were differentially labeled and then hybridized to the microarray described in panel A. The crosshairs represent the limit of measurement for the scanner.

FIG. 7A shows a plot of the normalized ratio of the channel intensities as a function of the intensity in one channel (Cy3) for each feature. For symmetry, we plotted the ratio of Cy5 to Cy3 channels above the median if greater than one, otherwise we plotted the inverse ratio below the median. There is a minimum scatter of ratios throughout a wide range of channel intensities: the ratios of channel intensity are approximately constant through-out the entire range. Only six ratios were outside of the range of 1.5, and none were outside 2.0. Essentially the same results were obtained in three separate experiments.

For comparison, we hybridized the same representation to itself. A single BglII representation was divided and separately labeled with Cy3 and with Cy5, mixed, and hybridized to an array of the same probes. FIG. 7B is plotted in the same manner as FIG. 7A. Note that there is no greater variation from the mean in the comparison of parallel representations than when we compare the identical sample. These experiments validate the extreme reproducibility of representations, and suggest that making well controlled parallel representations introduces no more noise than is inherent in the measurements made by the system as we practice it.

We also examined the reproducibility of our measurements of the differences between two different human breast cancer cell lines, SKBR-3 and MDA-MB-415. In these experiments, BglII representations of genomic DNA were made twice from each cell line. Pairs of representations were hybridized to 938 BglII probes, each printed in duplicate. We set minimum thresholds for channel intensity, averaged the Cy5/Cy3 ratios of duplicate features within each microarray, and graphed the values obtained from one experiment to those obtained from the other (see FIG. 8).

FIG. 8 shows the comparison of two microarray experiments. Parallel representations were produced for the two cell lines MDA-MB-415 and SKBR-3. These representations were differentially labeled and hybridized to an array of 938 features printed in duplicate. The ratios of duplicates were averaged and then graphed, the abscissa being the ratios from experiment 1 in ascending order (as an index) and the ordinate being the ratios from experiment 2 indexed in the same order as the abscissa.

In this experimental series, we observed greater than a twenty-five fold range of relative gene copy ratios, due to differences between the cell lines. There is excellent concordance between independent microarray measurements. Essentially similar results have been obtained in four independent series of experiments, using independent representations and independently printed microarrays. These experiments again attest to the reproducibility of representations, and also to the reproducibility of printing, labeling, and hybridization.

Verifiability of Microarray Data

Any measuring tool must also satisfy the criterion that it can be independently verified. We therefore sought confirmation of microarray measurements by quantitative Southern blotting of representations and genomic DNAs. For these studies, we used the cell lines SKBR-3 and MDA-MB-415. In all, we examined 36 non-repetitive probes that were concordant between two microarray experiments: 11 probes that reported significant differences in gene copy number between the cell lines, 15 probes that detected little or no difference, and 10 probes taken from a YAC that contains a region in 8q23 that we know to be amplified in SKBR-3. The blots were controlled for loading accuracy by stripping and rehybridization with control probes, and quantitated by scanning with a FUJIX BAS 2000 Bio-imaging Analyser.

FIGS. 9 A-D illustrate the analysis of 36 probes that displayed copy number differences from the previous experiment shown in FIG. 8 by Southern blotting representations and genomic DNA from the two cell lines MDA-MB-415 and SKBR-3. Some of the blots are shown. "M" designates MDA-MB-415 and "S" designates SKBR-3. Southern blots of representations (A, C, and D) or genomic DNA (B) are shown for probes with the designation "CHP" names. CHP0187 was a probe that detected no difference in copy number by array hybridization.

In general, array probes that detect differences between the cell lines, detect either of two types of events by Southern blotting: increased copy number in one of the cell lines, where there is appreciable signal from both (FIG. 9A and FIG. 9D); or the absence of signal from one cell line (FIG. 9C). The first type of event is likely to be gene amplification. The second type of event is likely to reflect gene deletion, either due to homozygous deletion or allelic loss of a polymorphic BglII site, with a small BglII fragment present in only one of the two cell lines. In fact, for five out of five cases of reported deletions, we concluded by PCR analysis that the difference between the cell lines was due to BglII polymorphism.

For the comparison of array and blot hybridization (FIG. 10), we plotted the inverse ratios when Southern blot analysis indicated gene loss for the cell line SKBR-3. FIG. 10 shows the ratios of gene copy number obtained by microarray measurement on the x-axis with ratios obtained by quantitative blotting of representations on the y-axis. Therefore, all deletions are plotted below 1, and amplifications plotted above 1. We have fit a straight line to the data by linear regression. It is evident that microarray hybridization underestimates the change in copy number for gene deletion. This most likely results from nonspecific background hybridization in the absence of specific hybridization.

There was good agreement between microarray data and the blotting data for 35 out of 36 probes. Only one probe was significantly discordant with the blotting data, a probe that consistently reported as amplified by microarray measurements but failed to report as amplified by Southern blotting of either representations or genomic DNA. We have no sure explanation for this anomalous probe, but it may detect a cross hybridizing DNA under the stringency of array hybridization that is not detected under the stringency of blot hybridization.

We also compared blots of representations with the blots of genomic DNA. We confirmed the fidelity of representation for thirteen of thirteen probes that were successfully analyzed both ways. A comparison of five blots of representations and companion blots of genomic DNA are shown in FIGS. 9A and 9B.

Experimental Comparison of Low and High Complexity Hybridization

We tested the role of complexity in array performance by a comparison of BglII and DpnII representations. Because all BglII sites (AGATCT) are also DpnII sites (GATC), our collection of microarrayed BglII fragments can be used as probes of DpnII representations, and because DpnII cleaves more frequently than BglII, a DpnII representation has higher complexity (about 70% of the genome) than a BglII representation (about 2.5%). These numbers were determined by cleaving in silico many megabases of known human genomic sequence, and determining the proportion of nucleotides in fragments 1.0 kbp or less, the sizes that are retained during representation. We compared BglII to DpnII representations of the two cell lines SKBR-3 and MDA-MB-415 by microarray hybridization. In these experiments we used a different set of arrayed probes, and larger numbers of probes, than used in the experiments reported in FIGS. 8, 9, and 10.

The results are strikingly clear when we make plots of ratios to single channel intensity (see FIGS. 11A, B and C).

FIGS. 11 A-C show the comparison of hybridizations of BglII representations to that of DpnII representations. Microarrays of 1658 features were hybridized, scanned, and threshed for intensity and the data was graphed in the same format as the data in FIGS. 7A, 7B, and 7C, with ratios (or inverse ratios) plotted as a function of single channel intensity. (A) BglII representations of the two cell lines MDA-MB-415 and SKBR-3 were differentially labeled and hybridized to arrays and graphed as described. (B) DpnII representations of the above cell lines were differentially labeled and hybridized to arrays analyzed and graphed as described. (C) The data from FIG. 11B was graphed at a smaller range to show scatter.

In these figures, deviation from the main line represents a detected change in copy number, with points above the main line reflecting higher copy numbers in SKBR-3, and points below reflecting higher copy number in MDA-MB-415. There is a dramatic increase both in the number of probes that detect change, as well as the degree of change they detect, when the low complexity representation is hybridized. Virtually none of the differences detected with BglII as decreased copy number in SKBR-3 can be detected with DpnII. Further analysis, not shown, indicates that a clear minority of probes detect differences by both types of representation.

We then compared the specific performance of probes derived from a YAC that localizes to 8q23 (see Table 2). Table 2 shows the comparison of ratios obtained from hybridizations of BglII and DpnII representations, for features located within one YAC. This YAC maps to 8q23, a region amplified in the cell line SKBR-3.

TABLE 2

| Name | Bgl Ratio | Dpn Ratio |
|---|---|---|
| CHP0140 | 5.43 | 0.98 |
| CHP0125 | 5.33 | 1.37 |
| CHP0218 | 3.86 | 1.25 |
| CHP0138 | 3.75 | 1.05 |
| CHP0121 | 3.37 | 1.23 |
| CHP0131 | 3.27 | 0.68 |
| CHP0134 | 3.25 | 1.06 |
| CHP0142 | 3.20 | 1.15 |
| CHP0120 | 2.97 | 1.38 |
| CHP0123 | 2.93 | 1.04 |
| CHP0215 | 2.53 | 1.04 |
| CHP0137 | 2.45 | 1.24 |
| CHP0132 | 1.76 | 1.03 |
| CHP0119 | 1.53 | 0.99 |
| CHP0136 | 0.9 | 0.96 |

This YAC derives from one of two regions residing near to but distinct from c-myc that we find commonly amplified in breast cancers (M Nakamura, unpublished). As can be seen from the data derived from the low complexity (BglII) representation, there are probes from this region which are highly amplified in SKBR-3 and probes which are not. One could use such data to delimit the epicenter of this amplification. One can infer from the high complexity (DpnII) representation that this region has undergone amplification, because the great majority of probes register ratios above the median. However, from the HCR data we do not have an appreciation of the degree of amplification that has occurred, and would be unable to delimit the epicenter of amplification.

Analysis of Microscopic Amounts of Tumor Biopsies.

We tested whether we could analyze small amounts of human tumor biopsies by microarray measurements. We chose a breast tumor, CHTN9, for which we also had data from representational difference analysis (RDA), Southern blotting of representations, and quantitative PCR (using TaqMan probes and ABI 7700 sequence detector). Because biopsies are a mixture of tumor and normal stroma, we flow sorted the nuclei from the biopsy into aneuploid and diploid fractions, and prepared BglII LCRs from 10,000 nuclei of each fraction.

We compared gene copy number between aneuploid (presumed tumor) and diploid (presumed normal) representations. In FIG. 7C, we plotted the ratio of the channel intensities, as a function of channel intensity in the normal channel for each feature (open circles). As in FIG. 7A, for symmetry, we plotted the tumor/normal ratio above the median if greater than 1.0, otherwise the normal/tumor ratio below the median. Thus amplifications are found above the main line, and deletions below the line. Because the scanner does not record above an intensity of 65,000 units, amplification will be underestimated at features that give strong signal in the normal channel. Lower luminosity excitation would collect more accurate data from these features. For the excitation luminosity setting of the experiment depicted in FIG. 7C, the points designated by cross hairs delimit the high intensity measurements of the scanner.

If we set a two fold difference in the ratio of median channel intensities for a feature to indicate probes that have undergone either amplification or deletion, there is excellent correlation between our microarray results and what we know about this tumor. All fifteen amplified probes that were found in these tumors by RDA, and confirmed by other means, were confirmed as amplified by our microarray analysis. Additional probes that derive from known amplified loci, but that have not yet been individually confirmed by other means, are also found amplified by microarray analysis. Moreover, probes that derive from loci that we know are not amplified in these tumors do not show amplification by microarray hybridization. Finally, five out of six probes found to be deleted by RDA, were also found to be deleted by microarray hybridization. Clearly, for CHTN9, our array data detects more amplifications than deletions. This is because the arrayed probes were weighted with probes from several loci that we know to be amplified in this tumor.

Discussion

We have demonstrated that hybridization of arrays of short (<1 kbp) DNA probes based on low complexity representations provides a method for detecting amplifications and deletions that is both reproducible and independently verifiable. We have demonstrated the analysis of microscopic amounts of tumor biopsy material using this method. In this report we have made LCRs using BglII cleavage, but our results are applicable to any system in which LCRs of samples are matched with an appropriate array of probes.

Our method has advantages in simplicity, flexibility, resolution and sample preparation. The simplicity is inherent in its design and the method for generating libraries of probes. The flexibility derives from having a virtually inexhaustible set of probes to use, so that probes with desirable characteristics can be selected. The resolution results from generally high specific to nonspecific hybridization signals for probes and is therefore limited only by the density of probes that can be printed. Additionally, because representations are used to prepare samples, only very minute amounts of starting material are needed.

Highly complex DNA samples can be analyzed by arrays of either short or long probes (Pinkel et al., 1998, *Nat. Genet.* 20: 207-211; Pollack et al., 1999, *Nat. Genet.* 23: 41-46), but signal to noise is problematic with short probes, and additional measures are required to establish reliability. In particular, Pollack et al. use "binning" which entails averaging signal over adjacent probes. We have simulated binning by 4 and 16 adjacent probes (data not shown). Binning by 4 gives a significant improvement in the detection of amplified sequences, but detection of deletion is still very problematic. Assuming the proper threshold could be determined, most amplifications can be safely discerned. Few if any, homozygous deletions could be safely called without also calling many false positives. Binning by 16 (data not shown), however, enables deletions to be readily recognized, and is comparable to analysis of BglII representations.

Although binning requires knowledge of the linkage of probes, similar enhancement could be achieved, in principle, merely by replica hybridizations. We call this "bundling". Bundling requires no knowledge of probe linkage. We have simulated bundling by 4 (data not shown). The result is very similar to binning by 4. There is a price to binning or bundling, however, that must be paid either as: a loss of genomic resolution in the detection of lesions; or, an increase in the number of probes used in the design of the chip; or, an increase in the number of replica hybridizations that must be performed.

One advantage of hybridizing arrays to representations is the ease of detecting allelic loss: representations are sensitive to nucleotide polymorphisms at the restriction endonuclease sites used in their preparation. For example, if normal DNA is heterozygous for a BglII site that creates a small BglII fragment, the loss of this site in the tumor is readily seen as a gene deletion. Since representations can also be made to be sensitive to polymorphisms at internal restriction endonuclease sites, it should be possible to intensively survey the cancer genome for allelic losses, or even mutational load. The same principles could be applied for whole genome genotyping of individuals by array hybridization. In fact, we showed that some of the gene copy number differences we detected between representations of two cell lines arise because of BglII polymorphisms.

It is often useful to distinguish loss of heterozygosity (allelic loss) from homozygous loss. This can be done by establishing dense probe "neighborhoods," that is, a linkage of nearby probes. Loss of heterozygosity (LOH) will be detected as a loss of signal from only a small subset of our probes, namely those that are capable of detecting BglII polymorphisms, and such probes will be sparsely distributed. Therefore, LOH will generally not cause the conjoint loss of signal from closely linked probes. On the other hand, if our probes are sufficiently dense, homozygous deletion will be marked by the conjoint loss of signal from closely linked probes.

Another advantage of genomic array hybridization emerges from linking data about the arrayed probes to the physical, genetic, and ultimately, the transcription map of the genome. Random representational probes do not have associated physical or genetic or transcriptional mapping information. However, this condition is very readily remedied. Representational probes can be mapped efficiently and placed into association in a variety of ways by hybridizing arrays of these probes to collections of YACs, BACs or radiation hybrids. Array hybridization to even unordered and unmapped pools of BACs, given sufficient numbers of probes and BACs, results in the assemblage of contigs of BACs and neighborhoods of probes with associated inferred physical distances.

We have described and illustrated the use of representational microarrays for the detection of gene copy number fluctuations in cancer. This tool also has other potential uses, including; measuring mutational load in cancers, monitoring DNA methylation patterns, genome wide genetic typing, and detection of de novo mutations in humans.

Experimental Procedures

Materials 96-well sterile and non-sterile plates were obtained from Corning-Costar, 96-well PCR plates were obtained from Marsh, *E. coli* strain XL1 Blue was obtained from Stratagene, BglII, DpnII and Ligase were supplied by New England Biolabs, Silanated glass slides were obtained from CEL Associates, Houston, Tex. Taq polymerase was 14 purchased from Perkin Elmer, and oligonucleotides were obtained from Operon Technologies. Pins (Chipmaker 2) used for the arrayer, and the hybridization chamber were purchased from Telechem International. Klenow fragment, Cy3 and Cy5, and dNTPs were obtained from Amersham Pharmacia Biotech.

Arraying

We used the Cartesian PixSys 5500 (Cartesian Technologies, Irvine, Calif.) to array our probe collections onto slides. We used a 2×2 pin configuration, and printed each probe in a center-to-center spacing of 280 mm in duplicate, yielding 8 quadrants or blocks. The dimensions of each printed array was 2 $cm^2$. Arrays were printed on commercially prepared silanated slides.

Probe Collection

BglII probes were obtained by several procedures. Initially, we obtained BglII probes that were the products of RDA experiments. Subsequently, we cloned small (<1.0 kbp) BglII fragments from BACs, P1s, and YACs obtained from various library resources (Research Genetics). Finally, we added to our collection by random cloning of small BglII fragments from the human genome. Probe fragments were maintained as pUC19 inserts in the *E. coli* strain XL1 Blue.

Preparation of Probes for Arraying

Arrays were made from two sets of probes, an early set with about 800 members, and a later set of about 2000. Glycerol stocks of the *E. coli* hosts were arrayed in 96 well plates. Probe preparation was started by PCR amplification of the insert directly from the lysed *E. coli* host, using primers set 1: pUC(for) aaggcgattaagttgggtaac and pUC(rev) caatttcacacaggaaacagc. 20 cycles of PCR (95° C. for 1 seconds, 55° C. for 30 seconds, and 72° C. for 1 minute) were followed by an extension of 10 minutes at 72° C. This created a stock for further amplifications 1 μl of this reaction was then used for a second PCR amplification to produce the probe fragments for arraying.

PCR amplification was carried out with primer set 2: M13 ttgtaaaacgacggccagtg and M13Rev ggaaacagctatgaccatga. These are internal to primer set 1, decreasing the possibility of *E. coli* contamination. The same PCR conditions were followed. PCR reactions were precipitated by addition of 1/10th volume of 3M NaAcetate (pH 5.3) and 1 volume of isopropanol. After 30 minutes at −20° C., the plates were centrifuges at 1500 rpm in a table top centrifuge. The supernatant was removed and the pellet was washed with 70% ethanol, centrifuged at 1500 rpm in a table top centrifuge for 5 minutes, and again the supernatant removed. The plates were dried in a vacuum oven, and then resuspended in 15 μl of 3×SSC for arraying.

Sample Preparation

Representations were prepared as described above in example 6.1. Briefly, DNA of choice was digested to completion with either BglII or DpnII, and cohesive adaptors were ligated to the digested ends. PCR primers complimentary to the adaptor ligated were then used for amplification by PCR. This product was then used for hybridization.

Labeling of Sample

10 μg of representation was denatured by heating to 95° C. in the presence of 5 μg of random nonamers in a total of 100 ul. After 5 minutes the sample was removed from heat and 20 ul of 5× buffer was added (50 mM Tris-HCL (pH 7.5), 25 mM $MgCl_2$, 40 mM DTT, supplemented with 33 μM dNTPs), 10 nmoles of either Cy3 or Cy5 was added, and the 4 units of Klenow fragment was added. After incubation of the reaction at 37° C. for 2 hours the reactions were combined and the incorporated probe was separated from the free nucleotide by centrifugation through a Microcon YM-30 column. The labeled sample was then brought up to 15 μl and a concentration of 3×SSC and 0.2% SDS, denatured and then hybridized to the array. Processing of the array. The array was placed in a humidified chamber for 3-5 minutes, until spots became hydrated. The slide was cross-linked by UV irradiation of 60 mJoules in a Stragene Stratlinker. The slide was then hydrated again in the humidified chamber and then snap dried by heating on the surface of a hot plate for several seconds. The array is then washed in 0.1% SDS for approximately 10 seconds, in deionized water for approximately 10 seconds, and then denatured in boiling deionized water for approximately 1-2 minutes. After denaturation the array is quickly immersed in ice cold benzene free ethanol for several seconds, taken out and allowed to dry. Cover slips for the arrays are put through the same wash procedure from the SDS to the ice cold ethanol. The 15 μl of sample is then placed on the array and a cover slip is slowly placed on the array.

Scanning, Informatics and Data Handling

Arrays were scanned by either GSI Lumonics ScanArray3000 or AxonGenePix4000. Feature definition and quantitative analysis of the resulting tiff files were performed with either ScanAlyze (Stanford University) or Axon GenePix2.0. The resulting tab-delimitated text files were then imported into S-plus 2000, a mathematics and statistical software package (MathSoft, www.mathsoft.com), with which we normalized the data and threshed by minimum intensity value of 300 to 500 depending on the average background pixel intensity. We implemented databases in Microsoft Access and used Perl for data extraction and reformatting.

The foregoing specification is considered to be sufficient to enable one skilled in the art to broadly practice the invention. Indeed, various modifications of the above-described methods for biochemistry, organic chemistry, medicine or related fields are intended to be within the scope of the following claims. All patents, patent applications, and publications cited are incorporated herein by reference in their entirety for all purposes.

What is claimed is:

1. A process for obtaining genomic copy number information about genomic DNA from a diseased cell of an organism, which does not involve Representational Difference Analysis (RDA), comprising a) providing a representation of the genomic DNA by digesting the genomic DNA from the diseased cell with a single restriction endonuclease to provide digested DNA fragments, ligating an adaptor to the digested DNA fragments to form ligated DNA fragments, and polymerase chain reaction (PCR) amplifying the ligated DNA fragments using a single set of primers complementary to the adaptor to provide the representation of the genomic DNA;

b) contacting nucleic acids from the representation provided in part (a), and a second representation obtained from genomic DNA from a normal cell from the same organism, with a microarray comprising i) a solid support with addresses of defined coordinates thereon; and ii) 1000 predetermined nucleic acid probes, wherein each probe has a different nucleic acid sequence; is affixed to an address of defined coordinates on the solid support; has 20 consecutive nucleotides in a sequence which is contained in the sequence of a member of said representation of part (a); and is mapped to a region of a genome, under conditions that allow hybridization between the nucleic acids and the nucleic acid probes to occur;

c) detecting the hybridization at addresses of defined coordinates of the microarray in step b), d) obtaining genomic copy number information based on the hybridization detected in step c).

2. The process of claim 1, wherein the genomic DNA is from a biopsy specimen, a cell line, an autopsy specimen, a forensic specimen or a paleontological specimen.

3. The process of claim 1, wherein the diseased cell is a tumor cell of an organism.

4. The process of claim 1, wherein the genomic DNA is from a non-tumor cell of an organism.

5. The process of claim 3, wherein the normal cell is a non-tumor cell from the same organism.

6. The process of claim 1, wherein the representation of step a) is fluorescently labeled.

7. The process of claim 1, wherein the microarray comprises 10,000 predetermined nucleic acid probes.

8. The process of claim 1, wherein the microarray comprises nucleic acid probes of 100-1000 nucleotides in length.

9. The process of claim 1, wherein the microarray comprises nucleic acid probes fixed to the surface of the solid support at their 5' ends.

10. The process of claim 1, wherein the microarray further comprises multiple copies of a probe, and wherein multiple copies of the same probe are affixed to an address.

11. The process of claim 1, wherein the microarray comprises a mixture of different nucleic acid probes affixed to an address.

12. The process of claim 1, wherein the probes at each address together have a total nucleotide complexity of less than or equal to 1.2 kb.

13. The process of claim 1, wherein the probes at each address together have a total nucleotide complexity that exceeds 1.2 kb.

14. The process of claim 1, wherein the representation of the genome has a complexity (R %) of 70%≥R %>0% of the complexity of the genome.

15. The process of claim 1, wherein the representation of the genome has a complexity (R %) of about 2%≥R %>0% of the complexity of the genome.

* * * * *